US012605555B2

(12) United States Patent
Wang

(10) Patent No.: US 12,605,555 B2
(45) Date of Patent: Apr. 21, 2026

(54) CARDIAC PACING THRESHOLD ACQUISITION METHOD, PACING CONTROL METHOD AND APPARATUS, AND MEDICAL DEVICE

(71) Applicant: UNITED INNOMED (SHANGHAI) LIMITED, Shanghai (CN)

(72) Inventor: Li Wang, Shanghai (CN)

(73) Assignee: UNITED INNOMED (SHANGHAI) LIMITED, Shanghai (CN)

( * ) Notice: Subject to any disclaimer, the term of this patent is extended or adjusted under 35 U.S.C. 154(b) by 274 days.

(21) Appl. No.: 18/270,499

(22) PCT Filed: Dec. 29, 2021

(86) PCT No.: PCT/CN2021/142654
§ 371 (c)(1),
(2) Date: Jun. 30, 2023

(87) PCT Pub. No.: WO2022/143800
PCT Pub. Date: Jul. 7, 2022

(65) Prior Publication Data
US 2024/0058614 A1 Feb. 22, 2024

(30) Foreign Application Priority Data

Dec. 30, 2020 (CN) .......................... 202011606453.0

(51) Int. Cl.
| | |
|---|---|
| *A61N 1/365* | (2006.01) |
| *A61B 5/352* | (2021.01) |
| *A61N 1/37* | (2006.01) |

(52) U.S. Cl.
CPC .......... *A61N 1/36592* (2013.01); *A61B 5/352* (2021.01); *A61N 1/3702* (2013.01); *A61N 1/371* (2013.01)

(58) Field of Classification Search
CPC ... A61N 1/36592; A61N 1/371; A61N 1/3712
See application file for complete search history.

(56) References Cited

U.S. PATENT DOCUMENTS

| | | | |
|---|---|---|---|
| 5,683,431 A | 11/1997 | Wang | |
| 5,766,230 A * | 6/1998 | Routh | .................. A61N 1/3712 |
| | | | 607/27 |

(Continued)

FOREIGN PATENT DOCUMENTS

| | | |
|---|---|---|
| CN | 101732795 A | 6/2010 |
| CN | 104797292 A | 7/2015 |

(Continued)

OTHER PUBLICATIONS

Feb. 2, 2024 Extended European Search Report issued in European Patent Application No. 21914532.3.

(Continued)

*Primary Examiner* — William J Levicky

(57) ABSTRACT

A cardiac pacing threshold acquisition method, a pacing control method and apparatus, and a medical device. The acquisition method comprises: in a pacing test phase, using an initial pacing frequency and an initial pacing output to perform pacing on a patient; under the pacing operation, measuring first response information of the ventricle of a patient to the initial pacing frequency; according to whether an R wave is present in the first response information, adjusting pulse voltage amplitude or pulse width of the initial pacing frequency so as to obtain a cardiac pacing threshold corresponding to the patient.

20 Claims, 9 Drawing Sheets

(56)　　　　References Cited

U.S. PATENT DOCUMENTS

| | | | |
|---|---|---|---|
| 7,437,190 B1 | 10/2008 | Hoberman et al. | |
| 2003/0078627 A1 | 4/2003 | Casavant et al. | |
| 2005/0137640 A1 | 6/2005 | Freeberg et al. | |
| 2014/0135867 A1* | 5/2014 | Demmer .............. | A61N 1/3712 607/28 |
| 2015/0119950 A1 | 4/2015 | Demmer et al. | |
| 2016/0206886 A1 | 7/2016 | Whiting et al. | |

FOREIGN PATENT DOCUMENTS

| | | |
|---|---|---|
| CN | 105873635 A | 8/2016 |
| CN | 107480414 A | 12/2017 |
| CN | 107537093 A | 1/2018 |
| CN | 109224298 A | 1/2019 |
| EP | 0334675 B2 | 3/2002 |
| JP | S5748223 B2 | 10/1982 |
| JP | 2005538800 A | 12/2005 |
| JP | 2015522318 A | 8/2015 |

OTHER PUBLICATIONS

Nov. 26, 2024 Second Office Action issued in Japanese Patent Application No. 2023-540639.

May 7, 2024 First Office Action issued in Japanese Patent Application No. 2023-540639.

Mar. 2, 2022 International Search Report issued in International Patent Application No. PCT/CN2021/142654.

Mar. 2, 2022 Written Opinion of the International Searching Authority issued in International Patent Application No. PCT/CN2021/142654.

Apr. 1, 2025 First Office Action issued in Chinese Patent Application No. 202011606453.0.

Jul. 8, 2025 Decision of Refusal issued in Japanese Patent Application No. 2023-540639.

Dec. 3, 2025 Second Office Action issued in Chinese Patent Application No. 202011606453.0.

* cited by examiner

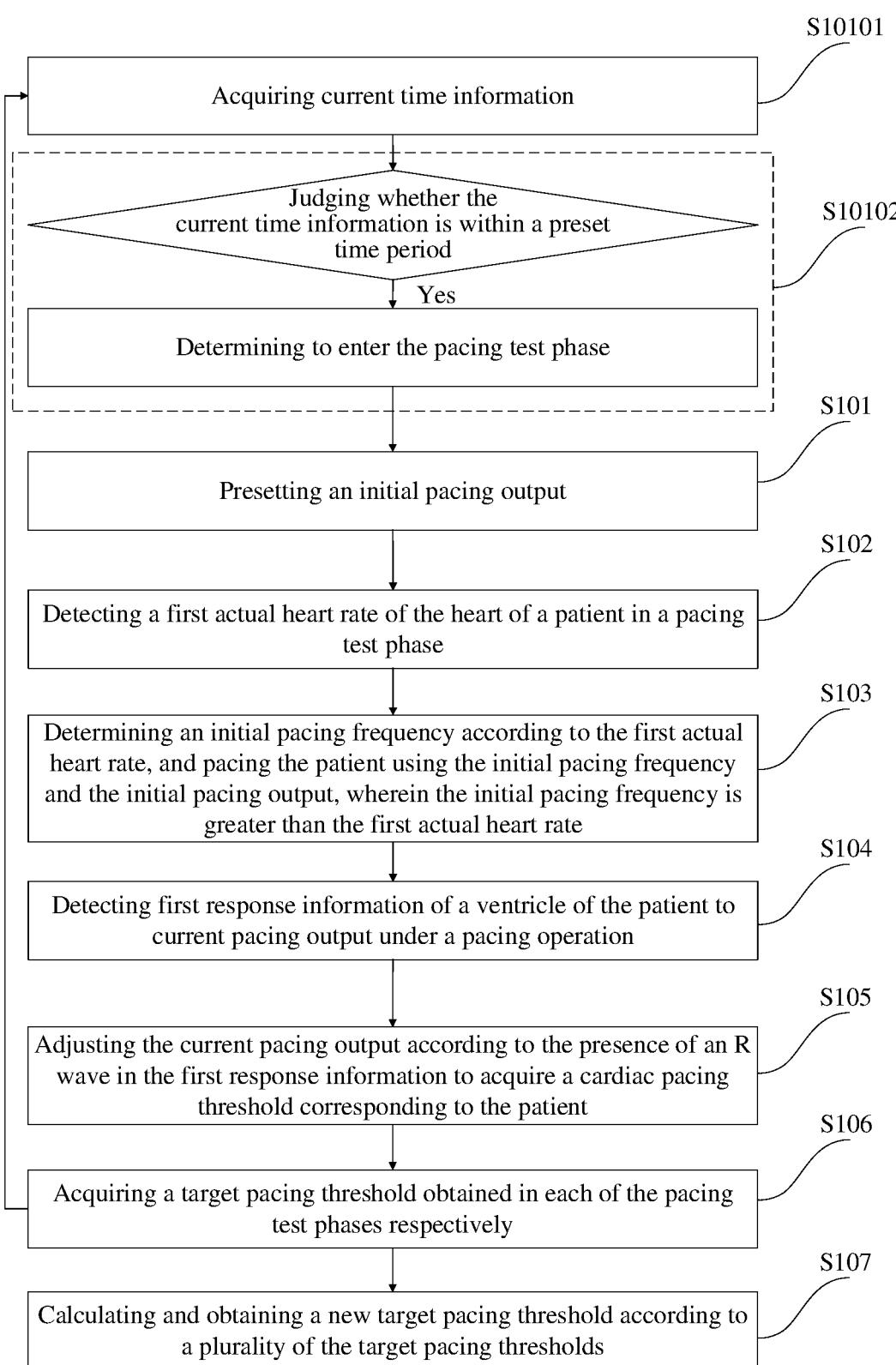

S10101

Acquiring current time information

Judging whether the
current time information is within a preset
time period

S10102

Yes

Determining to enter the pacing test phase

S101

Presetting an initial pacing output

S102

Detecting a first actual heart rate of the heart of a patient in a pacing
test phase

S103

Determining an initial pacing frequency according to the first actual
heart rate, and pacing the patient using the initial pacing frequency
and the initial pacing output, wherein the initial pacing frequency is
greater than the first actual heart rate

S104

Detecting first response information of a ventricle of the patient to
current pacing output under a pacing operation

S105

Adjusting the current pacing output according to the presence of an R
wave in the first response information to acquire a cardiac pacing
threshold corresponding to the patient

S106

Acquiring a target pacing threshold obtained in each of the pacing
test phases respectively

S107

Calculating and obtaining a new target pacing threshold according to
a plurality of the target pacing thresholds

FIG. 2

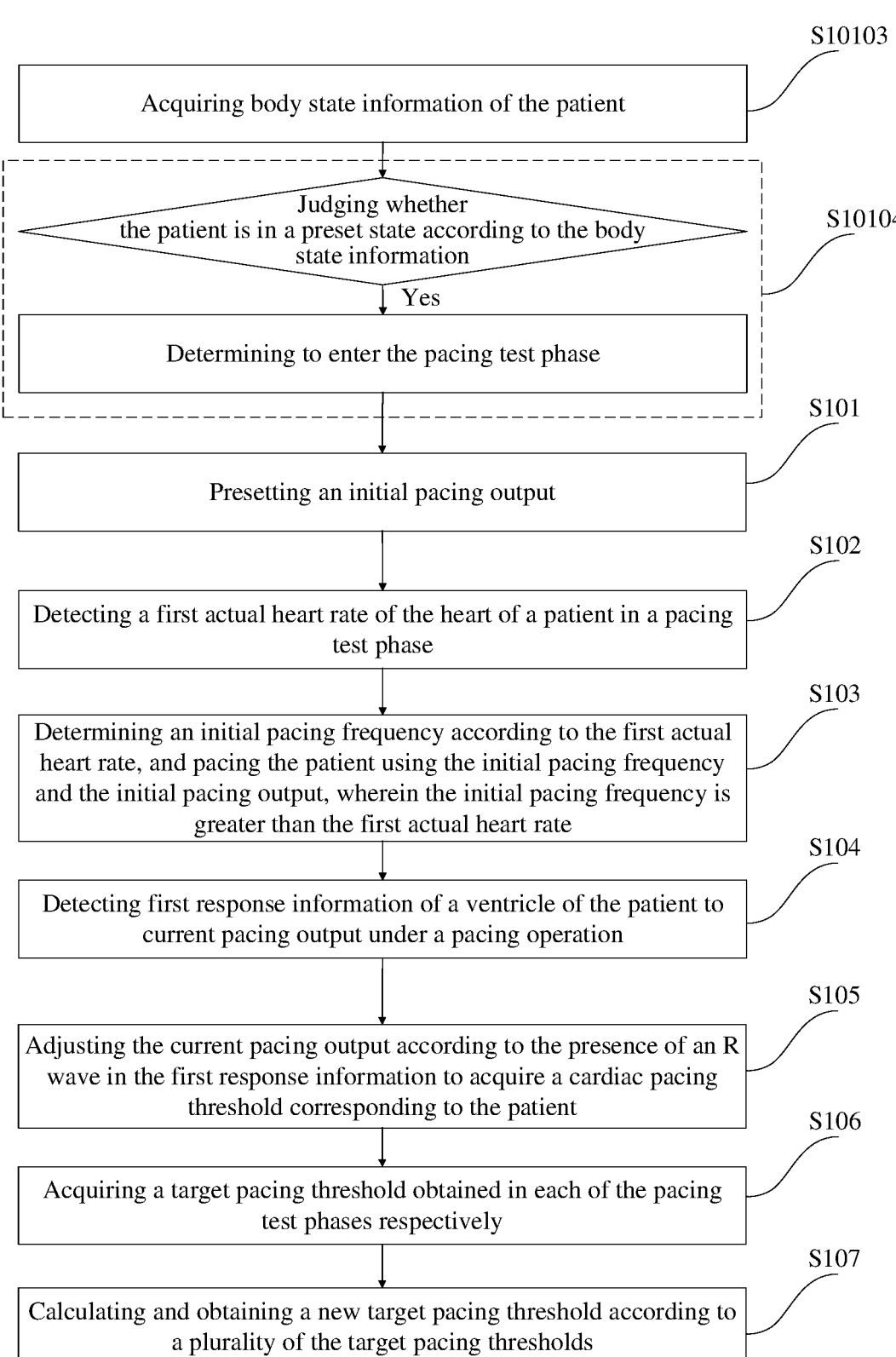

S10103

Acquiring body state information of the patient

S10104

Judging whether the patient is in a preset state according to the body state information Yes Determining to enter the pacing test phase

S101

Presetting an initial pacing output

S102

Detecting a first actual heart rate of the heart of a patient in a pacing test phase

S103

Determining an initial pacing frequency according to the first actual heart rate, and pacing the patient using the initial pacing frequency and the initial pacing output, wherein the initial pacing frequency is greater than the first actual heart rate

S104

Detecting first response information of a ventricle of the patient to current pacing output under a pacing operation

S105

Adjusting the current pacing output according to the presence of an R wave in the first response information to acquire a cardiac pacing threshold corresponding to the patient

S106

Acquiring a target pacing threshold obtained in each of the pacing test phases respectively

S107

Calculating and obtaining a new target pacing threshold according to a plurality of the target pacing thresholds

FIG. 3

CARDIAC PACING THRESHOLD ACQUISITION METHOD, PACING CONTROL METHOD AND APPARATUS, AND MEDICAL DEVICE

The present application is a National Stage of International Application No. PCT/CN2021/142654, filed on Dec. 29, 2021, which claims the priority of Chinese Patent Application No. 2020116064530 filed on Dec. 30, 2020, and the content of which is incorporated herein by reference in its entirety.

TECHNICAL FIELD

The present disclosure relates to the technical field of medical devices, and in particular to a cardiac pacing threshold acquisition method, a pacing control method and apparatus, and a medical device.

BACKGROUND

Real-time monitoring of a patient's heart rate, and performing timely cardiac pacing when the heart rate meets a given pacing condition to avoid too slow heart rate or even asystole (cardiac arrest) is one of the most basic purposes of a cardiac medical device (e.g., a cardiac pacemaker).

The existing pacing control modes are all based on a preset low-limit heart rate, i.e., to immediately use the same pacing output as the preset low-limit heart rate to pace the patient once the monitored patient's heart rate decreases to the preset low-limit heart rate, so as to prevent the heart rate of the patient from being lower than a set value and keep the heart rate of the patient to be not lower than the preset low-limit heart rate all the time.

However, the preset low-limit heart rate and the preset pacing output set in the existing pacing devices are fixed values summarized by doctors in clinical practice, that is, the pacing devices with the standardized pacing frequency and output are applied to different patients, and the pacing frequency and especially the output cannot be adapted to each patient according to different requirements (e.g., physical conditions and/or different times) of different patients, which results in poor user experience (the frequency does not meet the requirements or the output is too low to achieve the pacing effect) or low service life (for example, the output is too high), and cannot meet the higher use requirements of the patients.

In addition, when the existing pacing control mode is applied to uncommon endocardial/epicardial pacing, i.e., non-myocardial direct stimulation pacing, for example, percutaneous pacing (electrical stimulation), it can easily cause discomfort, such as pain, or even intolerable pain, to the patient; moreover, in the existing pacing control mode, pacing is started once the heart rate of the patient is reduced to a preset low-limit heart rate, then pacing operations are frequent, so that the patient is often in a painful state due to pacing operations, which causes problems like poor user experience, thereby reducing the patient's use of or compliance with the medical devices. Thus, some medical instruments that do not directly contact the heart/myocardium do not provide pacing therapy.

Content of the Present Invention

The present disclosure aims to overcome the defects that the prior art cannot perform specific pacing on different patients using adapted pacing output, and frequent pacing easily causes the patient to feel pain frequently leading to poor use experience, and provides a cardiac pacing threshold acquisition method, a pacing control method and apparatus, and a medical device, so that the pacing threshold can be known when human body requirements change, and the pacing output can achieve the pacing effect.

The present disclosure solves the above technical problems through the following technical solutions:

the present disclosure provides an acquisition method for a cardiac pacing threshold, the acquisition method comprising the following steps:

presetting an initial pacing output; wherein the initial pacing output comprises an initial pacing voltage amplitude and/or pulse width;

detecting a first actual heart rate of the heart of a patient in a pacing test phase;

determining an initial pacing frequency according to the first actual heart rate, and pacing the patient using the initial pacing frequency and the initial pacing output, wherein the initial pacing frequency is greater than the first actual heart rate;

detecting first response information of a ventricle of the patient to a current pacing output under a pacing operation; and adjusting the current pacing output according to occurrence situation of an R wave in the first response information to acquire a cardiac pacing threshold corresponding to the patient;

wherein when the heart rate state of the patient meets a pacing condition, preset pacing output outputted by a medical device is determined based on the cardiac pacing threshold, and the preset pacing output is greater than the cardiac pacing threshold.

By determining the initial pacing frequency based on the real-time heart rate state of each patient, the rationality and effectiveness of cardiac pacing threshold determination are ensured, and the efficiency of the cardiac pacing threshold determination is improved at the same time.

Generally, pacing heart rate (frequency)=self heart rate+x bpm, where x may be 5-15 bpm, and commonly x may be 10 bpm. That is, the patient is tested for pacing at a pacing heart rate slightly higher than the self heart rate of the patient to ensure the effectiveness and accuracy of the pacing operation and the test results.

By pacing the patient in the pacing test phase using the initial pacing frequency and the initial pacing output, the patient is synchronously detected for the occurrence situation of a corresponding R wave in the corresponding response information of the ventricle of the patient (e.g., the information represented in the electrocardiogram), and based on monitoring whether the R wave has occurred, pacing is performed using the pacing output adapted to each patient according to their different physical conditions, and the output is customized with the adaptive pacing energy, which ensures reasonable and effective pacing for different patients, effectively improves the pacing effect and the use experience of the patients, and at the same time, can also reduce the energy required for pacing, and extend the service time and lifespan of the instrument battery.

Preferably, the step of adjusting the current pacing output according to occurrence situation of the R wave in the first response information to acquire the cardiac pacing threshold corresponding to the patient comprises:

judging whether the R wave has occurred in the first response information, and if so, decreasing the current pacing output, and pacing the patient using the decreased pacing output;

detecting the first response information of the ventricle of the patient to the current pacing output under the pacing operation; and re-executing the step of decreasing the current pacing output when the R wave has occurred in the first response information until no R wave has occurred in the first response information and then taking a previous pacing output as the cardiac pacing threshold corresponding to the patient.

Preferably, the step of adjusting the current pacing output according to occurrence situation of an R wave in the first response information to acquire a cardiac pacing threshold corresponding to the patient comprises:

judging whether the R wave has occurred in the first response information, and if not, increasing the current pacing output, and pacing the patient using an increased pacing output;

detecting the first response information of the ventricle of the patient to the current pacing output under the pacing operation; and re-executing the step of increasing the current pacing output when no R wave has occurred in the first response information until the R wave has occurred in the first response information, and then taking the current pacing output as the cardiac pacing threshold corresponding to the patient.

Preferably, the step of pacing the patient using the initial pacing output comprises:

delivering the initial pacing output using a first electrode pair disposed in the medical device to pace the patient;

the step of detecting the first response information of the ventricle of the patient to the current pacing output under the pacing operation comprises:

sensing to obtain the first response information of the ventricle of the patient to the current pacing output using a second electrode pair disposed in the medical device;

wherein when the first electrode pair is a defibrillation electrode, the second electrode pair is a sensing electrode; or, when the first electrode pair is a sensing electrode, a pacing electrode or a defibrillation electrode, the second electrode pair is a defibrillation electrode.

In particular, in some medical instruments/devices, which use electrodes that are not in direct contact with the heart/myocardium, such as wearable cardioverter defibrillators (WCDs), external defibrillators (e.g., AEDs), subcutaneous implantable cardioverter defibrillators S-ICDs, etc., the first electrode pair (for pacing) is an electrode pair (with a relatively large area) configured in the devices to provide defibrillation energy for the heart of the patient; and the second electrode pair is a sensing electrode pair (with a relatively small area) configured in the devices to sense the electrical activity of the heart of the patient. Alternatively, the second electrode pair may also be an electrode pair (with a relatively large area) configured in the devices to provide defibrillation energy for the heart of the patient.

In some other medical instruments/devices, which use electrodes including those that are in direct contact with the myocardium, and are located within a cardiac vessel or chamber (e.g., implantable cardioverter defibrillators ICDs, etc.), the first electrode pair is an electrode pair configured in the instruments/devices to provide pacing energy for the heart of the patient; and the second electrode pair is an electrode pair (with a relatively large area) configured in the instruments/devices to provide defibrillation energy for the heart of the patient or an electrode pair configured to sense and/or provide pacing energy.

Preferably, when the R wave has occurred in the first response information, the acquisition method comprises:

acquiring the first response information of a second set number of ventricular pacing beat by beat after skipping the first response information of a first set number of ventricular pacing under the current pacing output;

determining that the current pacing output is ineffective when no R wave has occurred in the first response information of the ventricular pacing greater than a third set number, and increasing the current pacing output to pace the patient again, and then re-executing the step of acquiring the first response information of the second set number of ventricular pacing beat by beat after continuing to skip the first response information of the first set number of ventricular pacing under the current pacing output, wherein the third set number is smaller than or equal to the second set number;

determining that the current pacing output is effective when the R wave has occurred in the first response information of the ventricular pacing greater than a fourth set number, simultaneously decreasing the current pacing output, pacing the patient using the decreased pacing output, and re-executing the step of acquiring the first response information of the second set number of ventricular pacing beat by beat after skipping the first response information of the first set number of ventricular pacing until the R wave has occurred in the first response information of the ventricular pacing smaller than or equal to the third set number, and then determining that the current pacing output is ineffective, and determining that the previous pacing is effective, and taking a pulse voltage amplitude and/or pulse width of the previous pacing as the cardiac pacing threshold, wherein the fourth set number is smaller than or equal to the second set number; and otherwise, continuing to acquire the first response information of the second set number of ventricular pacing beat by beat and analyzing the occurrence situation of the R wave until the cardiac pacing threshold is acquired.

Preferably, when the different pacing test phases are preset, the acquisition method further comprises:

acquiring the cardiac pacing threshold obtained in each of the pacing test phases respectively; and performing an average calculation or a weighted average calculation based on a plurality of the cardiac pacing thresholds to obtain a new cardiac pacing threshold.

Preferably, before the step of pacing the patient using the initial pacing frequency and the initial pacing output, the method further comprises:

acquiring current time information, judging whether the current time information is within a preset time period, and if so, determining to enter the pacing test phase; and/or acquiring body state information of the patient, judging whether the patient is in a preset state (including a general sleep state or a specific sleep state such as deep sleep) according to the body state information, and if so, determining to enter the pacing test phase.

The present disclosure also provides a pacing control method, the pacing control method comprising the following steps:

acquiring a second actual heart rate of the heart of a patient;

judging whether the second actual heart rate meets a preset low heart rate condition, and if so, performing cardiac pacing on the patient using a preset pacing frequency and a preset pacing output; wherein the preset low heart rate condition is used for representing that the patient is in a life-threatening state; and detecting second response information of a ventricle of the patient to the preset pacing output under a pacing operation, judging whether an R wave has occurred in the second response information, and if so, determining that the preset pacing output is effective, and continuing to pace the patient using the preset pacing output; otherwise, determining that the preset pacing output is ineffective, and adjusting the preset pacing output to pace the patient using the adjusted pacing output; or, performing a pacing-triggered cardiac contractility modulation on the patient; or, detecting the second response information of the ventricle of the patient to the preset pacing output under the pacing operation, judging whether the R wave has occurred in the second response information, and if so, determining that the preset pacing output is effective, and continuing to pace the patient using the preset pacing output, and simultaneously performing an R wave-triggered cardiac contractility modulation on the patient.

The cardiac pacing threshold involved in the pacing control method of the present disclosure may be determined based on an existing acquisition mode in the prior art, or may be obtained by using the above acquisition method for the cardiac pacing threshold in the present disclosure, and may be specifically selected or adjusted according to an actual scene.

Whether an R wave has occurred in the response information of the ventricle of the patient under cardiac pacing is monitored in time to determine the effectiveness of the cardiac pacing output, increasing the pacing output in time for pacing when the pacing output is ineffective until the pacing output can enable the R wave to be present in the response information, in order to achieve the effect of effectively pacing the patient to restore blood circulation as soon as possible.

The patient can be paced in a critical state, and CCM (cardiac contractility modulation) stimulation is added to achieve the effect of better supporting the heartbeat and blood circulation of the patient to restore the heart of the patient to normal.

In addition, the patient, when in a critical state, can be subjected to cardiac pacing using the preset pacing frequency and preset pacing output, and the patient is subjected to R wave-triggered CCM modulation when the R wave is monitored to be present in the response information of the ventricle of the patient under cardiac pacing after pacing, that is, based on a processing scheme combining the pacing output, the detection of the R wave and the CCM cardiac contractility modulation, the treatment effect on the patient is greatly improved, and the timeliness and effectiveness of restoring the heartbeat of the patient to normal are ensured. If the patient occasionally has his own heartbeat during pacing, the CCM modulation is triggered by sensing the R wave.

Preferably, the step of adjusting the preset pacing output to pace the patient using the adjusted pacing output comprises:

increasing a current pacing output, and pacing the patient using the increased pacing output;

detecting the second response information of the ventricle of the patient to the current pacing output under the pacing operation; and re-executing the step of increasing the current pacing output when no R wave has occurred in the second response information until the R wave has occurred in the second response information, and then pacing the patient using the increased current pacing output, and taking the current pacing output as the cardiac pacing threshold corresponding to the patient.

Preferably, the pacing control method further comprises:

pacing the patient using a maximum pacing output of a medical device when the number of times of increasing the preset pacing output is greater than a set number of times, and/or a time length of adjusting the preset pacing output exceeds a set time length.

Preferably, the step of judging whether the R wave has occurred in the second response information, if so, determining that the preset pacing output is effective, and continuing to pace the patient using the preset pacing output; otherwise, determining that the preset pacing output is ineffective, and adjusting the preset pacing output to pace the patient using the adjusted pacing output comprises:

acquiring the second response information after each pacing beat by beat under the current pacing output, and judging whether the R wave has occurred in the second response information after each pacing, and if so, determining that the preset pacing output is effective, and continuing to pace the patient using the preset pacing output; and if not, determining that the preset pacing output is ineffective, increasing the current pacing output at a current pacing moment and pacing the patient using the increased pacing output, and continuing to execute the step of acquiring the second response information of each pacing output beat by beat until acquiring an effective pacing output which enables the R wave to be present in the second response information of each pacing output; or, the step of detecting the second response information of the ventricle of the patient to the preset pacing output under the pacing operation, judging whether the R wave has occurred in the second response information, and if so, determining that the preset pacing output is effective, and continuing to pace the patient using the preset pacing output, and simultaneously performing the R wave-triggered cardiac contractility modulation on the patient comprises:

acquiring the second response information after each pacing beat by beat under the current pacing output, and judging whether the R wave has occurred in the second response information after each pacing, and if so, determining that the preset pacing output is effective, and continuing to pace the patient using the preset pacing output, and simultaneously performing the R wave-triggered cardiac contractility modulation on the patient.

Preferably, the step of judging whether the R wave has occurred in the second response information, if so, determining that the preset pacing output is effective, and continuing to pace the patient using the preset pacing output; otherwise, determining that the preset pacing output is ineffective, and adjusting the preset pacing output to pace the patient using the adjusted pacing output comprises:

judging whether the R wave has occurred in the second response information after a first pacing under the current pacing output, and if so, determining that the preset pacing output is effective, and continuing to pace the patient using the preset pacing output; if not, pacing the patient using the increased pacing output after the set time length until acquiring the effective pacing output which enables the R wave to be present in the second response information of each pacing; or, the step of detecting the second response information of the ventricle of the patient to the preset pacing output under the pacing operation, judging whether the R wave has occurred in the second response information, and if so, determining that the preset pacing output is effective, and continuing to pace the patient using the preset pacing output, and simultaneously performing the R wave-triggered cardiac contractility modulation on the patient comprises:

judging whether the R wave has occurred in the second response information after the first pacing under the current pacing output, and if so, determining that the preset pacing output is effective, and continuing to pace the patient using the preset pacing output, and simultaneously performing the R wave-triggered cardiac contractility modulation on the patient.

The present disclosure also provides an acquisition apparatus for a cardiac pacing threshold, the acquisition apparatus comprising:

a pacing output presetting module, configured to preset an initial pacing output;

wherein the initial pacing output comprises an initial pacing voltage amplitude and/or pulse width;

a heart rate acquisition module, configured to detect a first actual heart rate of the heart of a patient in a pacing test phase;

a pacing module, configured to determine an initial pacing frequency according to the first actual heart rate, and pace the patient using the initial pacing frequency and the initial pacing output, wherein the initial pacing frequency is greater than the first actual heart rate;

a response information detection module, configured to detect first response information of a ventricle of the patient to a current pacing output under a pacing operation; and a first judgment module, configured to adjust the current pacing output according to occurrence situation of an R wave in the first response information to acquire a cardiac pacing threshold corresponding to the patient;

wherein when the heart rate state of the patient meets a pacing condition, a preset pacing output which is output by a medical device is determined based on the cardiac pacing threshold, and the preset pacing output is greater than the cardiac pacing threshold.

Preferably, the first judgment module is configured to judge whether the R wave has occurred in the first response information, and if so, decrease the current pacing output, and call the pacing module to pace the patient using the decreased pacing output;

the response information detection module is configured to detect the first response information of the ventricle of the patient to the current pacing output under the pacing operation;

the first judgment module is configured to decrease the current pacing output again when the R wave has occurred in the first response information, and call the pacing module to pace the patient using the decreased pacing output; and the first judgment module is further configured to take previous pacing output as the cardiac pacing threshold corresponding to the patient when no R wave has occurred in the first response information.

Preferably, the first judgment module is configured to judge whether the R wave has occurred in the first response information, and if not, increase the current pacing output, and call the pacing module to pace the patient using the increased pacing output;

the response information detection module is configured to detect the first response information of the ventricle of the patient to the current pacing output under the pacing operation;

the first judgment module is further configured to increase the current pacing. output again when no R wave has occurred in the first response information, and call the pacing module to pace the patient using the increased pacing output; and the first judgment module is further configured to take the current pacing output as the cardiac pacing threshold corresponding to the patient when the R wave has occurred in the first response information.

Preferably, the pacing module is configured to deliver the initial pacing output to pace the patient using a first electrode pair disposed in the medical device; and the response information detection module is configured to sense and obtain the first response information of the ventricle of the patient to the current pacing output by using a second electrode pair disposed in the medical device;

wherein when the first electrode pair is a defibrillation electrode, the second electrode pair is a sensing electrode; or, when the first electrode pair is a sensing electrode, a pacing electrode or a defibrillation electrode, the second electrode pair is a defibrillation electrode.

Preferably, the pacing module is configured to, under the current pacing output, skip the first response information of a first set number of ventricular pacing, and then acquire the first response information of a second set number of ventricular pacing beat by beat;

determining that the current pacing output is ineffective when no R wave has occurred in the first response information of the ventricular pacing greater than a third set number, and increasing the current pacing output to pace the patient again, and then re-executing the step of acquiring the first response information of the second set number of ventricular pacing beat by beat after continuing to skip the first response information of the first set number of ventricular pacing under the current pacing output, wherein the third set number is smaller than or equal to the second set number;

when the R wave has occurred in the first response information of the ventricular pacing greater than a fourth set number, the current pacing output is determined to be effective, the current pacing output is simultaneously decreased, the patient is paced using the decreased pacing output, and the step of skipping the first response information of the first set number of ventricular pacing, and then acquiring the first response information of the second set number of ventricular pacing beat by beat is re-executed until the R wave has occurred in the first response information of the ventricular pacing smaller than or equal to the third set number, and the current pacing output is then determined to be ineffective, and the previous pacing is determined to be effective, and the pulse voltage amplitude and/or pulse width of the previous pacing is taken as the cardiac pacing threshold, wherein the fourth set number is smaller than or equal to the second set number; and otherwise, continuing to acquire the first response information of the second set number of ventricular pacing beat by beat and analyzing the occurrence situation of the R wave until the cardiac pacing threshold is acquired.

Preferably, when different pacing test phases are preset, the acquisition apparatus further comprises:

a threshold acquisition module, configured to acquire the cardiac pacing threshold obtained in each of the pacing test phases respectively; and a threshold calculation module, configured to perform an average calculation or a weighted average calculation based on a plurality of the cardiac pacing thresholds to obtain a new cardiac pacing threshold.

Preferably, the acquisition apparatus further comprises:

a time information acquisition module, configured to acquire current time information; and a second judgment module, configured to judge whether the current time information is within a preset time period, and if so, determine to enter the pacing test phase; and/or the acquisition apparatus further comprises:

a state information acquisition module, configured to acquire body state information of the patient; and a third judgment module, configured to judge whether the patient is in a preset state according to the body state information, and if so, determine to enter the pacing test phase.

The present disclosure also provides a pacing control apparatus, the pacing control apparatus comprising:

a heart rate acquisition module configured to acquire a second actual heart rate of the heart of a patient;

a fourth judgment module, configured to judge whether the second actual heart rate meets a preset low heart rate condition, and if so, perform cardiac pacing on the patient using a preset pacing frequency and the preset pacing output; wherein the preset low heart rate condition is used for representing that the patient is in a life-threatening state; and a response information detection module, configured to detect second response information of a ventricle of the patient to the preset pacing output under a pacing operation; wherein the first judgment module is configured to judge whether an R wave has occurred in the second response information, and if so, determine that the preset pacing output is effective, and continue to call the pacing module to pace the patient using the preset pacing output; otherwise, determine that the preset pacing output is ineffective, and adjust the preset pacing output to call the pacing module to pace the patient using the adjusted pacing output; or, an adjustment module, configured to perform a pacing-triggered cardiac contractility modulation on the patient; or, the response information detection module is configured to detect the second response information of the ventricle of the patient to the preset pacing output under the pacing operation; the first judgment module is configured to judge whether the R wave has occurred in the second response information, and if so, determine that the preset pacing output is effective, continue to call the pacing module to pace the patient using the preset pacing output, and call the adjustment module to perform an R wave-triggered cardiac contractility modulation on the patient.

The cardiac pacing threshold in the pacing control apparatus of the present disclosure may be determined based on an existing acquisition mode in the prior art, or may be obtained by using an acquisition mode corresponding to the above cardiac pacing threshold acquisition apparatus of the present disclosure, and specifically may be selected or adjusted according to an actual scene.

Preferably, the first judgment module is configured to increase the current pacing output and call the pacing module to pace the patient using the increased pacing output;

the response information detection module is configured to detect the second response information of the ventricle of the patient to the current pacing output under the pacing operation;

the first judgment module is further configured to increase the current pacing output again when no R wave has occurred in the second response information, and call the pacing module to pace the patient using the increased pacing output; and the first judgment module is further configured to call the pacing module to pace the patient using the increased current pacing output when the R wave has occurred in the second response information, and take the current pacing output as the cardiac pacing threshold corresponding to the patient.

Preferably, the pacing module is further configured to pace the patient using a maximum pacing output of the medical device when the number of times of increasing the preset pacing output is greater than a set number of times, and/or time length of adjusting the preset pacing output exceeds the set time length.

Preferably, under the current pacing output, the response information detection module is configured to acquire the second response information of each ventricular pacing beat by beat;

the first judgment module is configured to judge whether the R wave has occurred in the second response information of each ventricular pacing, and if so, determine that the preset pacing output is effective, and continue to call the pacing module to pace the patient using the preset pacing output;

if not, determine that the preset pacing output is ineffective, the pacing module is called to increase the current pacing output at the current heartbeat time and pace the patient using the current pacing output, and the response information detection module is called until effective pacing output which enables the R wave to be present in the second response information of each ventricular pacing is acquired; or, under the current pacing output, the response information detection module is configured to acquire the second response information after each pacing beat by beat; and the first judgment module is configured to judge whether the R wave has occurred in the second response information of each ventricular pacing, and if so, determine that the preset pacing output is effective, continue to call the pacing module to pace the patient using the preset pacing output, and call the adjustment module to perform the R wave-triggered cardiac contractility modulation on the patient.

Preferably, under the current pacing output, the first judgment module is configured to judge whether the R wave has occurred in the second response information of the first ventricular pacing, and if so, determine that the preset pacing output is effective, and continue to call the pacing module to pace the patient using the preset pacing output; if not, the pacing module is called to pace the patient using the increased pacing output after the set time length until the effective pacing output which enables the R wave to be present in the second response information of each ventricular pacing is acquired; or, under the current pacing output, the first judgment module is configured to judge whether the R wave has occurred in the second response information of the first ventricular pacing, and if so, determine that the preset pacing output is effective, continue to call the pacing module to pace the patient using the preset pacing output, and call the adjustment module to perform the R wave-triggered cardiac contractility modulation on the patient.

The present disclosure also provides a medical device, the medical device comprising the above pacing control apparatus.

Preferably, the medical device comprises a wearable cardioverter defibrillator (WCD), an external defibrillator (e.g., AED), an external temporary pacemaker, an implantable cardioverter defibrillator ICD, a subcutaneous implantable cardioverter defibrillator S-ICD, or a mechanical circulatory support device MCS.

The positive and progressive effects of the present disclosure are as follows:

(1) by pacing the patient in different pacing test phases (such as the patient being in a deep sleep state) using the initial pacing output, whether the R wave has occurred in the response information corresponding to the ventricle of the patient is synchronously detected, the pacing output is continuously increased when no R wave has occurred or the pacing output is continuously decreased when the R wave has occurred until the pacing output which just can trigger the occurrence situation of the R wave is obtained, so that based on monitoring whether the R wave has occurred, pacing is performed using the pacing output adapted to each patient according to different physical conditions of different patients, and the output is customized with the adaptive pacing output energy, which ensures reasonable and effective pacing for different patients, effectively improves the use experience of the patients, and at the same time, can also reduce the energy required for pacing, and extend the service time and lifespan of the instrument battery. In addition, the patient is in a critical state (i.e., the patient is in severe bradycardia or cardiac arrest), the CCM is triggered by pacing when the patient is paced using the preset pacing frequency and the preset pacing output, or R wave-triggered CCM modulation is performed on the patient when the R wave is monitored to be present in the response information of the ventricle of the patient under the cardiac pacing, so that the treatment effect on the patient is greatly improved, and the timeliness and the effectiveness of restoring the heartbeat of the patient to normal are improved.

(2) the pacing test is performed on the patient regularly or irregularly over time to dynamically update the cardiac pacing threshold, so that the physical changes of the patient can be timely tracked to obtain the pacing output adaptive to the latest physical condition of the patient, which further ensures reasonable and effective pacing for the patient, further enhances the use experience of the patient, and simultaneously reduces the energy required for pacing, and extends the service time and lifespan of the instrument battery.

(3) the present disclosure is not only aiming at patients with bradycardia in the traditional sense, but also taking patients in life-threatening states with severe bradycardia or even cardiac arrest caused by basic or acute heart disease as the objects needing pacing support; pacing is performed on the patient using the pacing output of the set pacing output only under the condition of necessary pacing, such that the effect of timely and effective pacing to support the life of the patient is achieved, and the pacing is stopped when the heart rate of the patient recovers to a certain degree; in daily use, the patient also achieves a great degree of avoiding unnecessary pacing, and reducing the effect of pain caused by pacing stimulation, so that the acceptance, compliance, and use experience of users on the medical instruments are improved. This is of great significance for external emergency instruments or devices that currently do not have pacing function (e.g., WCDs, external defibrillators, temporary pacemakers, etc.) and subcutaneous instruments (e.g., SICDs). In the occurrence of sudden cardiac death, a considerable portion begins with severe bradycardia or cardiac arrest, and the timely pacing (percutaneous or subcutaneous) can save the lives of patients in time, like external defibrillation (for VT/VF). Meanwhile, as the patient has already fainted during the attack, restoring the heartbeat becomes a main contradiction, and if this type of pacing causes pain to the patient, it will not be felt at this time, let alone the main contradiction.

(4) when the patient (particularly a patient in life crisis due to cardiac arrest or severe bradycardia) is paced using the set pacing frequency and output, timely multi-beat or beat-by-beat detection is carried out on whether the R wave has occurred in the response information of the ventricle of the patient to determine the effectiveness of the cardiac pacing output, and the pacing output is increased timely to pace when the cardiac pacing output is ineffective until the R wave has occurred in the response information due to the pacing output, so that the effect of effectively pacing the patient as soon as possible to provide blood circulation capable of maintaining life is achieved; when the pacing output adjustment times or time length exceeds a certain range, the maximum pacing output is used for pacing to ensure that the heart of the patient can rapidly and efficiently obtain the effective pacing output as much as possible; in addition, once new pacing output which can be used for successful pacing is acquired, the pacing output (pulse voltage amplitude and/or pulse width) is saved for future pacing, and the effect of intelligent pacing is achieved.

BRIEF DESCRIPTION OF THE DRAWINGS

FIG. 2 is a first flowchart of an acquisition method for a cardiac pacing threshold according to Embodiment 2 of the present disclosure.

FIG. 3 is a second flowchart of an acquisition method for a cardiac pacing threshold according to Embodiment 2 of the present disclosure.

DETAILED DESCRIPTION OF THE PREFERRED EMBODIMENT

The present disclosure is further illustrated by the embodiments below, which are not intended to limit the present disclosure to the scope of the embodiments.

Embodiment 1

Figure 1:
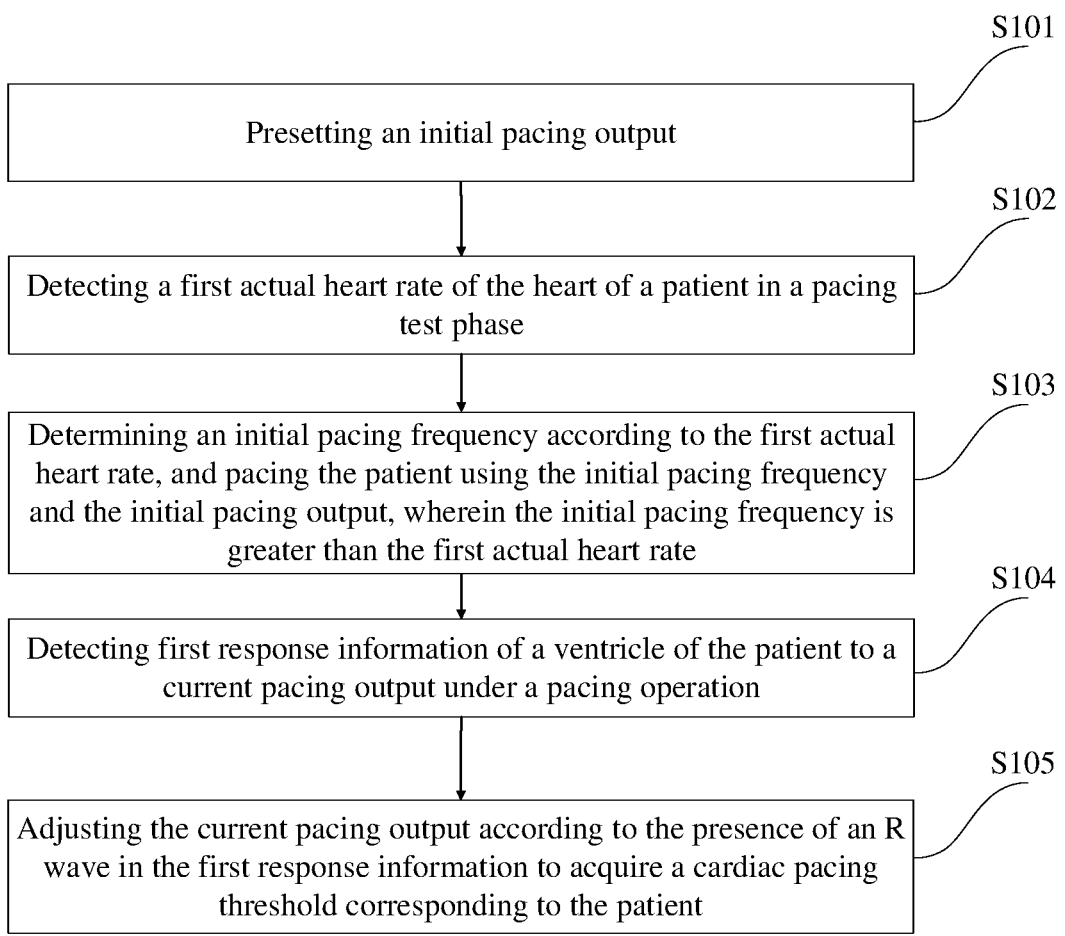
FIG. 1 is a flowchart of an acquisition method for a cardiac pacing threshold according to Embodiment 1 of the present disclosure.

As shown in FIG. 1, the acquisition method for a cardiac pacing threshold according to this embodiment includes:

S101, presetting an initial pacing output; wherein the initial pacing output includes an initial pacing voltage amplitude and/or pulse width;

S102, detecting a first actual heart rate of the heart of a patient in a pacing test phase;

S103, determining an initial pacing frequency according to the first actual heart rate, and pacing the patient using the initial pacing frequency and the initial pacing output, wherein the initial pacing frequency is greater than the first actual heart rate;

By determining the initial pacing frequency based on the real-time heart rate state of each patient, the rationality and effectiveness of cardiac pacing threshold determination are ensured, and the efficiency of the cardiac pacing threshold determination is improved at the same time.

Generally, pacing heart rate (frequency)=self heart rate+x bpm, where x may be 5-15 bpm, and commonly x may be 10 bpm. That is, the patient is tested for pacing at a pacing heart rate slightly higher than the self heart rate of the patient to ensure the effectiveness and accuracy of the pacing operation and the test results.

Where the pacing test phase may be a time period (e.g., two or three o'clock in the morning) during which the patient is in a deep sleep state, and the pacing device automatically triggers the pacing test to acquire the cardiac pacing threshold. It is certain that the pacing test phase may be reset and adjusted according to the work and rest time or usage habits of different patients.

S104, detecting first response information of a ventricle of the patient to a current pacing output under a pacing operation;

wherein a ventricular response can be reflected by, but not limited to, a body surface, subcutaneous, endocardial, epicardial electrocardiogram.

S105, adjusting the current pacing output according to the occurrence situation of an R wave in the first response information to acquire a cardiac pacing threshold corresponding to the patient;

wherein when the heart rate state of the patient meets a pacing condition, preset pacing output which is output by the medical instrument/device is determined based on the cardiac pacing threshold, and the preset pacing output (pulse voltage amplitude and/or pulse width) is larger than the cardiac pacing threshold. Where if no cardiac pacing threshold exists at present, the pacing output preset by the medical instrument when leaving a factory or manually by a doctor is used.

The cardiac pacing threshold is a value determined according to different physical conditions of different patients, each patient is paced with pacing output adapted to the patient by acquiring the cardiac pacing threshold, so that the effect of customizing the output with the adaptive pacing output is achieved, and the rationality and effectiveness of pacing output setting are ensured.

In addition, the automatic pacing test can be performed on the patient regularly or irregularly over time based on the doctor's advice on the patient's use or the patient's usage habits and adaptability and the like to dynamically update the cardiac pacing threshold, so that the body and the state of illness of the patient can be tracked timely to obtain the pacing output adapted to the latest condition of the patient, which further ensures reasonable and effective pacing for the patient, further enhances the use experience of the patient; and simultaneously reduces the energy required for pacing, and extends the service time and lifespan of the instrument battery.

In this embodiment, by using the initial pacing output to pace the patient in the pacing test phase, whether the R wave has occurred in the response information corresponding to the ventricle of the patient is synchronously detected, and based on monitoring whether the R wave has occurred, pacing is performed using the pacing output that is adapted to each patient according to different physical conditions of different patients, and the output is customized with the adaptive pacing output, which ensures reasonable and effective pacing for different patients, and effectively improves the use experience of the patients.

Embodiment 2

The acquisition method for a cardiac pacing threshold according to this embodiment is a further improvement of Embodiment 1, specifically:

as shown in FIG. 2, the step S101 follows the steps:

S10101, acquiring current time information; and

S10102, judging whether the current time information is within a preset time period, and if so, determining to enter the pacing test phase.

That is, by setting a certain time (e.g., a certain time period of each day) as a pacing test time, once the set time is reached, the pacing device automatically enters the pacing test phase to automatically acquire the current cardiac pacing threshold corresponding to the patient.

Alternatively, as shown in FIG. 3, the step S101 follows the steps:

S10103, acquiring body state information of the patient; and

S10104, judging whether the patient is in a preset state (including being in a general sleep state or a specific sleep state such as deep sleep) according to the body state information, and if so, determining to enter the pacing test phase.

That is, when the patient is in the sleep state, such as the deep sleep at two or three o'clock in the morning, the pacing device automatically enters the pacing test phase, and automatically acquires the current cardiac pacing threshold corresponding to the patient without affecting the normal daily life or night sleep, avoiding uncomfortable experience of the patient and ensuring the comfort in use for the patient.

It is certain that the pacing device may also be automatically triggered to enter the pacing test procedure according to other set conditions, as long as the cardiac pacing threshold can be acquired effectively in time, and therefore, the details are not repeated here.

When different pacing test phases are preset, the step S105 is followed by the steps:

S106, acquiring the cardiac pacing threshold obtained in each of the pacing test phases respectively; and S107, calculating and obtaining a new cardiac pacing threshold according to a plurality of the cardiac pacing thresholds.

Specifically, the new cardiac pacing threshold is obtained by performing calculations such as an average calculation or a weighted average calculation based on the plurality of the cardiac pacing thresholds.

Different cardiac pacing thresholds corresponding to the same patient in the same time period and/or different time periods are obtained by setting a plurality of pacing test phases, and then a final cardiac pacing threshold is obtained by comprehensively calculating the plurality of the cardiac pacing thresholds, that is, the accuracy of the cardiac pacing threshold is further ensured by combining a plurality of groups of data.

This embodiment uses defibrillation electrodes, including but not limited to those provided in the medical device, to deliver pacing energy to pace the patient, specifically:

delivering the initial pacing output using a first electrode pair disposed in the medical device to pace the patient;

the step of detecting the first response information of the ventricle of the patient to the current pacing output under the pacing operation comprises:

sensing to obtain the first response information of the ventricle of the patient to the current pacing output using a second electrode pair disposed in the medical device;

wherein when the first electrode pair is a defibrillation electrode, the second electrode pair is a sensing electrode; or, when the first electrode pair is a sensing electrode, a pacing electrode or a defibrillation electrode, the second electrode pair is a defibrillation electrode.

In particular, in some medical instruments/devices, which use electrodes that are not in direct contact with the heart/myocardium, such as wearable cardioverter defibrillators (WCDs), external defibrillators (e.g., AEDs), external temporary pacemakers, subcutaneous implantable cardioverters S-ICDs, etc., the first electrode pair (for pacing) is an electrode pair (with a relatively large area) originally configured to provide defibrillation energy for the heart of the patient; and the second electrode pair is a sensing electrode pair (with a relatively small area) configured in the devices to sense the electrical activity of the heart of the patient. Alternatively, the second electrode pair may also be an electrode pair (with a relatively large area) configured in the devices to provide defibrillation energy for the heart of the patient.

In some other medical instruments/devices, which use electrodes including those that are in direct contact with the myocardium, and are located within a cardiac vessel or chamber (e.g., implantable cardioverter defibrillators ICDs, etc.), the first electrode pair is an electrode pair originally configured to provide pacing energy for the heart of the patient; and the second electrode pair is an electrode pair (with a relatively large area) originally configured in the devices to provide defibrillation energy for the heart of the patient, or an electrode pair configured to sense and/or provide pacing energy.

In particular, the medical instruments/devices in this embodiment require the provision of a sensing electrode pair (sensing the R wave) for sensing cardiac activity and a defibrillation electrode pair for implementing pacing. By providing different electrode pairs for cardiac activity sensing and pacing, as exemplified by a WCD or AED, pacing energy is output through external defibrillation electrodes (the first electrode pair) placed on the skin of the patient and is indirectly transmitted to the heart (myocardium) through the chest wall and other tissues. Pacing energy is preferably transmitted through two large surface area defibrillation electrodes, such as one electrode placed on the left side of the anterior chest (near the apex region) and the other electrode placed on the posterior chest (left side), preferably at the level of the anterior chest electrode or slightly above it, wherein the position arrangement relationship of the electrode pairs and the principle of cooperative operation belong to mature technologies in the art and therefore are not described in detail herein. The electrical signals of cardiac activity are sensed by the distinct, second electrode pair (sensing electrode pair), such as a body surface electrocardiogram (ECG) electrode, placed on the skin of the patient. The sensed cardiac electrical activity is used in an algorithm to determine whether and when pacing is needed, etc. When pacing is performed by the defibrillation electrodes, the sensing electrode pair determines whether pacing is effective by sensing an R wave of the electrocardiogram.

In a preferred embodiment, to minimize the influence of pacing energy on the electrocardiographic sensing circuitry, the two ECG (electrocardiogram) electrodes (i.e., sensing electrodes) are preferably placed in close proximity (e.g., in the range of 1-2 cm); the two sensing electrodes are parallel to one edge of the two large surface area defibrillation electrodes, and the R wave measured by the sensing electrodes during sinus rhythm should be as large as possible, at least above a certain value, such as 0.5 mV. In addition, the defibrillation electrodes with large surface areas for transmitting pacing pulses may also be used to sense the R wave, and a high-energy protection circuit is needed to ensure that the influence of pacing energy on the sensing circuit is minimized as much as possible to ensure that the R wave can be effectively detected in real time, wherein the use of the high-energy protection circuit to minimize pacing energy is a mature technology in the art and therefore is not described in detail herein.

For a subcutaneously implanted apparatus, such as an SICD, pacing energy is transmitted to the heart (myocardium) through subcutaneous electrodes placed outside the heart and thorax (the thorax and associated muscles and other tissues), through the thorax and associated tissues. The SICD senses cardiac electrical activity through electrodes placed under the skin (outside the heart and thorax) of the patient, and the sensed electrocardiographic R wave is used in the algorithm to determine whether and when pacing is needed. When pacing is performed by the defibrillation electrodes, the sensing electrode pair determines whether pacing is effective by sensing an R wave of the electrocardiogram.

For an apparatus implanted intravenously in vivo, such as an ICD, electrocardiographic sensing and pacing energy are, when needed, typically transmitted directly to the heart (myocardium) by electrodes placed inside the heart (commonly the right ventricular intima or left ventricular adventitia). During pacing, the ICD may sense cardiac electrical activity by forming a sensing electrode pair with defibrillation electrodes placed in the superior vena cava and right ventricle of the patient, an ICD housing placed under the chest skin and defibrillation electrodes placed in the right ventricle, or an ICD housing under the chest skin and defibrillation electrodes placed in the superior vena cava, and the sensed electrocardiographic R wave is used in the algorithm to determine whether pacing is effective. CRT (cardiac resynchronization therapy) can also sense the post-pacing cardiac electrical activity (the R wave) by assembling sensing electrode sets with other non-pacing electrodes. For example, during right ventricular pacing, the left ventricular electrode may be used to sense cardiac electrical activity (the post-pacing R wave). And vice versa.

In addition, those skilled in the art may configure sensing electrodes for sensing cardiac activity and pacing electrodes for pacing in other cardiac devices/instruments such as an MCS according to actual requirements, and the specific number and arrangement modes of the defibrillation electrodes for defibrillation are not limited as long as monitoring of cardiac activity and energy output of the patient can be achieved respectively. These electrodes may constitute a pacing electrode pair (the first electrode pair) and a sensing electrode pair (the second electrode pair) to achieve pacing threshold management. For example, adding pacing and/or defibrillation function to the MCS system may provide treatment in the event of severe bradycardia or VT/VF, while providing a mechanism for pacing threshold measurement and management (similar to that described above) through the use of an energy output electrode (pacing or defibrillation electrode) and a sensing electrode pair. These MCS devices have hardware to provide mechanical support for the heart and control algorithms and energy sources, and additional pacing/defibrillation functions may also be configured and implemented and therefore are not described in detail herein.

Figure 4:
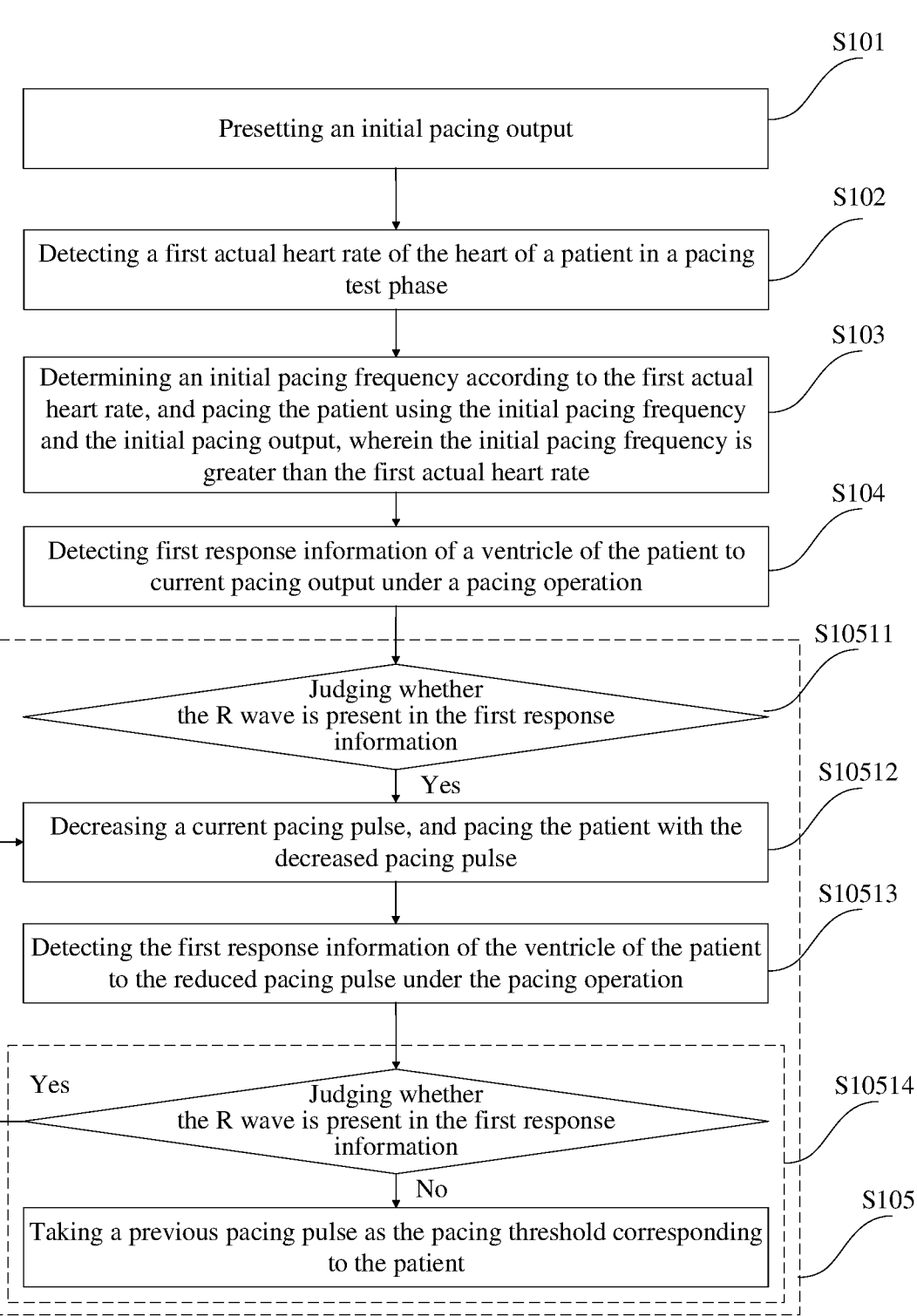
FIG. 4 is a third flowchart of an acquisition method for a cardiac pacing threshold according to Embodiment 2 of the present disclosure.

As shown in FIG. 4, the step S105 includes:

S10511, judging whether the R wave has occurred in the first response information, and if so, executing step S10512;

S10512, decreasing the current pacing output, and pacing the patient using the decreased pacing output;

S10513, detecting first response information of a ventricle of the patient to a current pacing output under a pacing operation;

S10514, judging whether the R wave has occurred in the first response information, and if so, re-executing the step S10512; if not, taking a previous pacing output as the cardiac pacing threshold corresponding to the patient.

That is, if the R wave has occurred in the response of the current pacing output acting on the ventricle of the patient, it indicates that the current pacing output can effectively pace the patient and that a case of being too high may exist, at this time, the patient is paced again by decreasing the pacing output step by step, and if the R wave continues to be present in the response of the ventricle of the patient, the pacing output continues to be decreased until no R wave has occurred in the response of the ventricle of the patient, and then it indicates that the current pacing output is too low, and the previous adjusted pacing output is determined to be the cardiac pacing threshold corresponding to the patient.

The pacing output can be further refined and adjusted between the current pacing output and the previous pacing output to obtain a more accurate cardiac pacing threshold, specifically, how to refine and adjust it can be preset, and certainly, the refining and adjusting mode can also be reset and adjusted according to actual requirements.

In addition, in order to acquire the cardiac pacing threshold more matched with the patient, the adjusting mode of the pacing output can be further optimized, for example, the amplitude of two adjacent pacing outputs is adjusted in a mode of decreasing by a large span first and then decreasing by a small span, so that the speed and the accuracy of acquiring the cardiac pacing threshold are ensured; or the amplitude of two adjacent pacing outputs is adjusted in a mode of decreasing by the small span all the time, so that the accuracy of the cardiac pacing threshold is effectively ensured. It is certain that technical solutions based on other adjusting modes of pacing output may also be used, as long as the cardiac pacing threshold corresponding to the patient can be finally obtained, and therefore, the details are not described herein.

Figure 5:
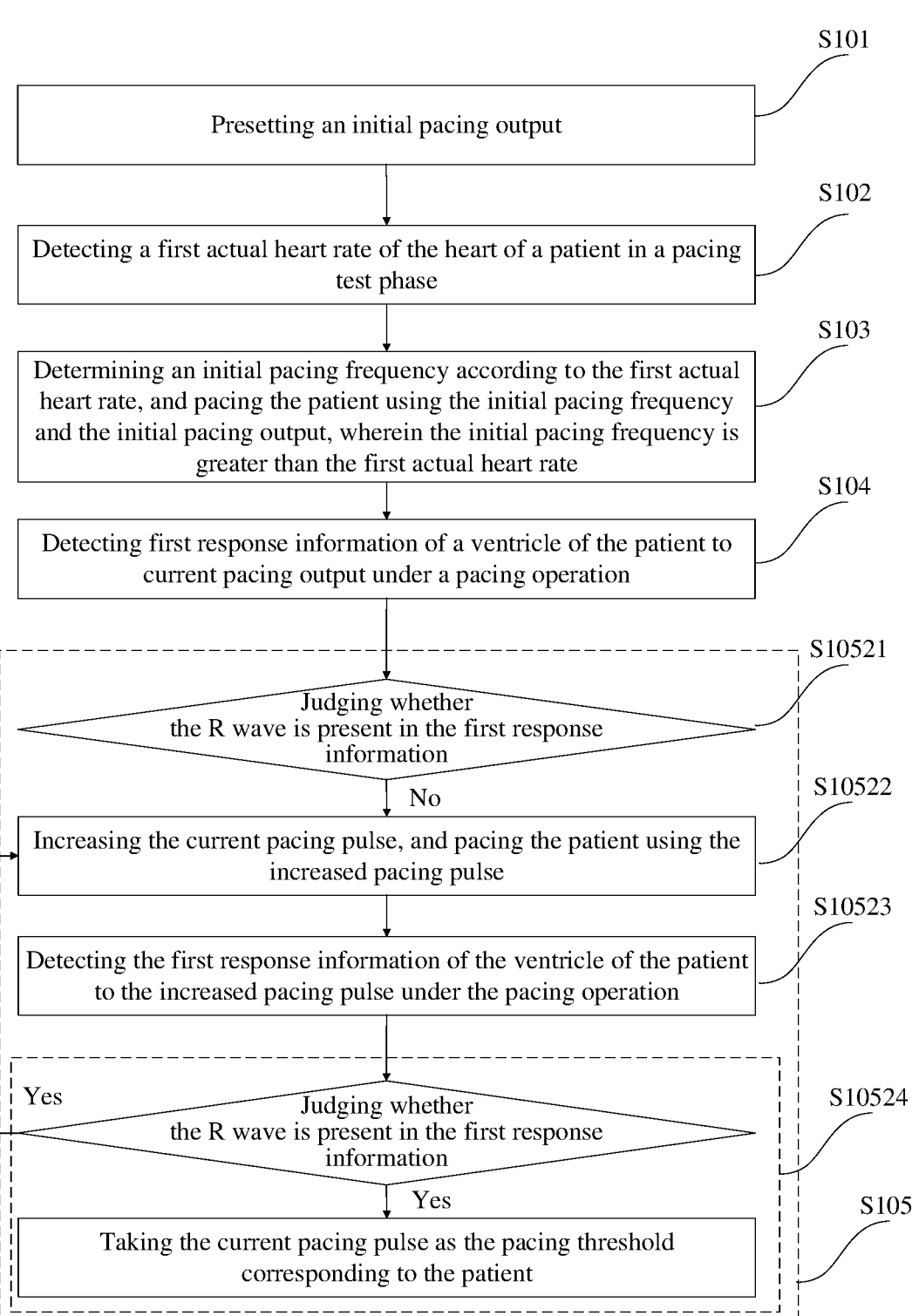
FIG. 5 is a fourth flowchart of an acquisition method for a cardiac pacing threshold according to Embodiment 2 of the present disclosure.

Alternatively, as shown in FIG. 5, the step S105 includes:

S10521, judging whether the R wave has occurred in the first response information, and if not, executing step S10522;

S10522, increasing the current pacing output, and pacing the patient using an increased pacing output;

S10523, detecting first response information of a ventricle of the patient to a current pacing output under a pacing operation;

S10524, judging whether the R wave has occurred in the first response information, and if not, re-executing the step S10522; if so, taking the current pacing output as the cardiac pacing threshold corresponding to the patient.

That is, if no R wave has occurred in the response of the current pacing output acting on the ventricle of the patient, it indicates that the current pacing output cannot perform effective pacing on the patient, at this time, the patient is paced again by increasing the pacing output step by step, and if no R wave continues to be present in the response of the ventricle of the patient, the pacing output continues to be increased until the R wave has occurred in the response of the ventricle of the patient, and then it indicates that the current pacing output is too low, and the previous adjusted pacing output is determined to be the cardiac pacing threshold corresponding to the patient.

Where the pacing output can be further refined and adjusted between the current pacing output and the previous pacing output to obtain a more accurate cardiac pacing threshold, specifically, how to refine and adjust it can be preset, and certainly, the refining and adjusting mode can also be reset and adjusted according to actual requirements.

In addition, in order to acquire the cardiac pacing threshold more matched with the patient, the adjusting mode of the pacing output can be further optimized, for example, the amplitude of two adjacent pacing outputs is adjusted in a mode of increasing by a large span first and then increasing by a small span, so that the speed and the accuracy of acquiring the cardiac pacing threshold are ensured; or the amplitude of two adjacent pacing outputs is adjusted in a mode of increasing by the small span all the time, so that the accuracy of the cardiac pacing threshold is effectively ensured. It is certain that technical solutions based on other adjusting modes of pacing output may also be used, as long as the cardiac pacing threshold corresponding to the patient can be finally obtained, and therefore, the details are not described herein.

Specifically, in order to further improve the accuracy of determining the cardiac pacing threshold corresponding to the patient, the step of adjusting the current pacing output according to occurrence situation of the R wave in the first response information to acquire the cardiac pacing threshold corresponding to the patient includes:

judging whether the R wave has occurred in the first response information, and if not, increasing the current pacing output, and pacing the patient using the increased pacing output;

detecting first response information of a ventricle of the patient to a current pacing output under a pacing operation; and when no R wave has occurred in the first response information, the step of increasing the current pacing output is re-executed until the R wave has occurred in the first response information, and the current pacing output is then decreased, and the decreased pacing output is used to pace the patient;

detecting first response information of a ventricle of the patient to a current pacing output under a pacing operation; and re-executing the step of decreasing the current pacing output when the R wave has occurred in the first response information until no R wave has occurred in the first response information and then taking the previous pacing output as the cardiac pacing threshold corresponding to the patient.

That is, when the current pacing output is too high, the current pacing output is decreased (the decreased span can be dynamically adjusted according to the specific situation, that is, the span adjusted each time can be consistent or inconsistent) step by step, and when the current pacing output is too low, the current pacing output is increased (the increased span can be dynamically adjusted according to the specific situation, that is, the span adjusted each time can be consistent or inconsistent) step by step, and multiple dynamic adjustments, combined with the occurrence situation of the R wave after each adjustment, ultimately determine the cardiac pacing threshold of the current patient, further ensuring the accuracy and effectiveness of cardiac pacing threshold determination, and thus ensuring the rationality and effectiveness of pacing work in the subsequent pacing therapy process.

In an optional technical solution, a multi-beat detection approach is adopted to reasonably determine the cardiac pacing threshold that is really adapted to the patient, and the specific processing procedure is as follows:

when the R wave has occurred in the first response information detected after the current pacing output is decreased, the acquisition method includes:

acquiring the first response information of a second set number of ventricular pacing beat by beat after skipping the first response information of a first set number of ventricular pacing under the current pacing output;

determining that the current pacing output is ineffective when no R wave has occurred in the first response information of the ventricular pacing greater than a third set number, and increasing the current pacing output to pace the patient again, and then re-executing the step of under the current pacing output, acquiring the first response information of the second set number of ventricular pacing beat by beat after skipping the first response information of the first set number of ventricular pacing, wherein the third set number is smaller than or equal to the second set number;

determining that the current pacing output is effective when the R wave has occurred in the first response information of the ventricular pacing greater than a fourth set number, simultaneously decreasing the current pacing output, pacing the patient using the decreased pacing output, and re-executing the step of acquiring the first response information of the second set number of the ventricular pacing beat by beat after skipping the first response information of the first set number of the ventricular pacing until the R wave has occurred in the first response information of the ventricular pacing smaller than or equal to the third set number, and then determining that the current pacing output is ineffective, and determining that the previous pacing output is effective, and taking the pulse voltage amplitude and/or pulse width of the previous pacing output as the cardiac pacing threshold, wherein the fourth set number is smaller than or equal to the second set number; and otherwise, continuing to acquire the first response information of the second set number of ventricular pacing beat by beat and analyzing the occurrence situation of the R wave until the cardiac pacing threshold is acquired.

For example, after a certain pacing output is output, the response condition corresponding to the first three beats is firstly ignored, then the response condition of the 4th to 6th beats is directly judged, and when the response information of the 4th to 6th beats indicates that the R wave has occurred in each beat, the current pacing output is determined to be effective; when the response information of the 4th to 6th beats indicates that no R wave has occurred in the three beats, the current pacing output is determined to be ineffective; otherwise, the response condition corresponding to the three beats from the current beat is continuously acquired and analyzed, wherein the specific analysis process is the same as the above process, and therefore the detailed description is omitted. It is certain that the multi-beat detection mode can be adjusted according to actual situations.

In this embodiment, the initial pacing output and the initial pacing output are used for pacing the patient in the pacing test phase, whether the R wave has occurred in the response information corresponding to the ventricle of the patient is synchronously detected, and the pacing output is continuously increased when no R wave has occurred or the pacing output is continuously decreased when the R wave has occurred until the pacing output (the cardiac pacing threshold) which just can trigger the R wave to be present is obtained, so that based on monitoring whether the R wave has occurred, pacing is performed using the pacing output adapted to each patient according to different physical conditions of different patients, and the output is customized with the adaptive pacing output, so that reasonable and effective pacing for different patients is ensured, and the use experience of the patients is effectively improved; in addition, the cardiac pacing threshold is dynamically updated, so that reasonable and effective pacing for the patients is further ensured, and the use experience of the patients is further improved.

Embodiment 3

The cardiac pacing threshold involved in the pacing control method according to this embodiment may be determined based on an existing acquisition mode in the prior art, or may be obtained by using the above cardiac pacing threshold acquisition method of the present disclosure, and may be specifically selected or adjusted according to an actual scene.

Figure 6:
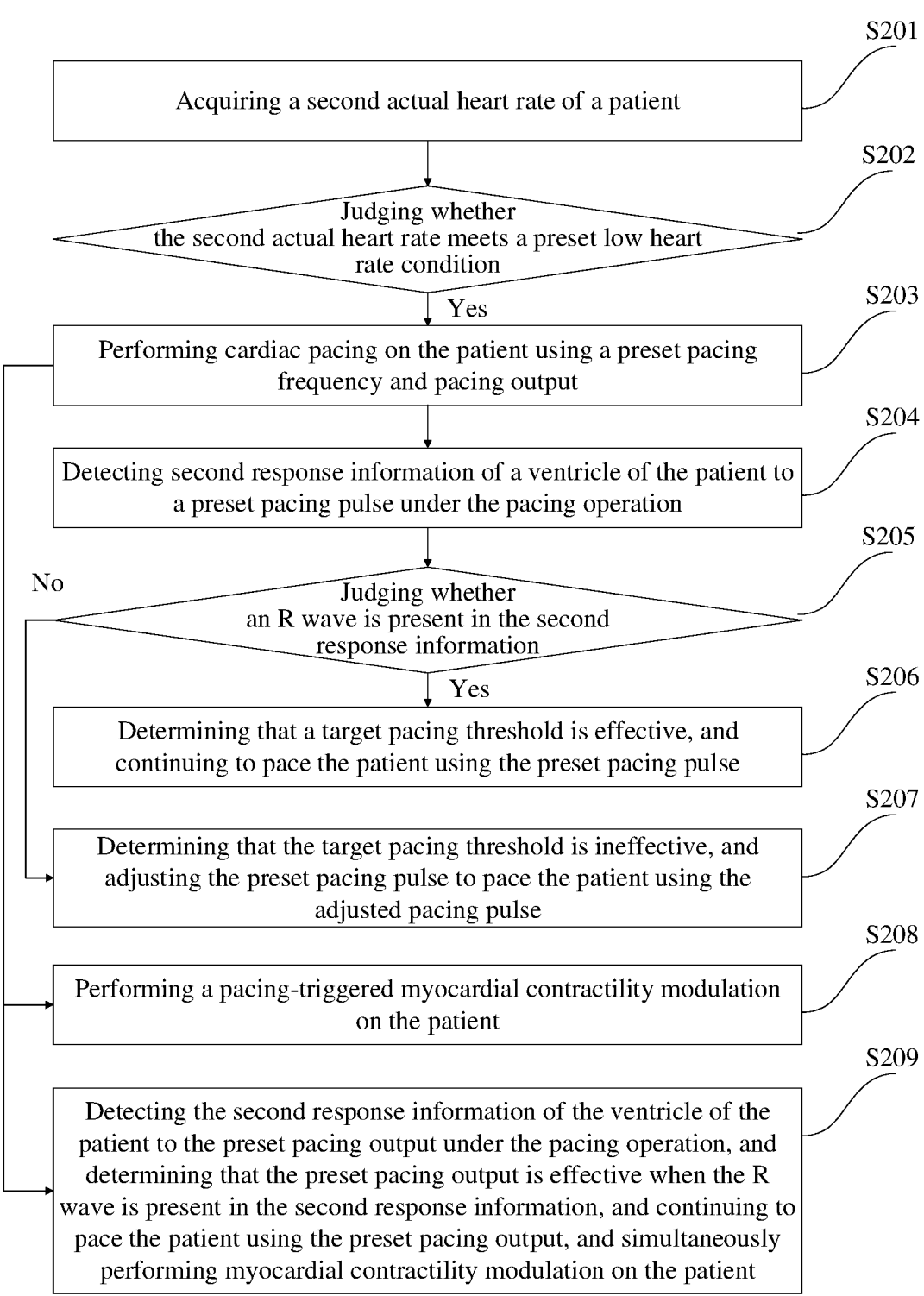
FIG. 6 is a flowchart of a pacing control method according to Embodiment 3 of the present disclosure.

As shown in FIG. 6, the pacing control method according to this embodiment includes:

S201, acquiring a second actual heart rate of the heart of a patient;

S202, judging whether the second actual heart rate meets a preset low heart rate condition, and if so, executing step S203; and S203, performing cardiac pacing on the patient using a preset pacing frequency and pacing output;

wherein the preset low heart rate condition is used for representing that the patient is in a life-threatening state.

The method is not only used for patients suffering from bradycardia in the traditional sense, but also used for patients suffering from severe bradycardia or even cardiac arrest caused by basic or acute heart disease, and patients in the foregoing life-threatening states are taken as objects needing pacing support, who are likely to die without pacing (patients in urgent need of assistance), that is, the pacing operation in the present disclosure is only implemented in a "last resort"/"life-saving" situation.

Specifically, the triggering condition for implementing the pacing operation is preset, so that the patient is paced using higher pacing output only under the condition of necessary pacing, and the effect of timely and effective pacing to support the life of the patient is achieved; meanwhile, in daily use, the patient also achieves a great degree of avoiding unnecessary pacing and reducing the effect of pain caused by pacing stimulation, so that the acceptance, compliance, and use experience of users on the medical instruments are improved.

The preset pacing frequency can be set according to the actual experience value of a doctor to achieve the effect of emergency pacing for life saving. In addition, the historical effective pacing frequency corresponding to the current patient can be used as the initial pacing frequency of the medical device.

Specifically, the step S202 includes:

judging whether the second actual heart rate is smaller than a preset low heart rate, and if so, executing the S203.

By monitoring the real-time heart rate of the patient, when the real-time heart rate is smaller than the preset low heart rate (far smaller than the preset low limit heart rate in the existing pacing control mode), the condition that the patient is in urgent need of assistance is determined, that is, the cardiac pacing for the patient is triggered only when the heart rate of the patient is very low, and the effect of timely and effective pacing to support the life of the patient is achieved. Alternatively, the step S202 includes:

judging whether the second actual heart rate is smaller than a preset low heart rate, and if so, acquiring the duration of a first low heart rate of the heart of the patient in the second actual heart rate; and judging whether the duration of the first low heart rate reaches time length of the preset low heart rate, and if so, executing the step S203.

Real-time monitoring of real-time heart rate of the patient rate triggers pacing only when the second actual heart rate is less than the preset low heart rate and the duration of the first low heart rate of the second actual heart rate reaches the time length of the preset low heart rate, avoiding the occurrence of unnecessary pacing operations caused by the heart rate of the patient accidentally falling below the preset low heart rate, so that better pacing monitoring function is achieved, and the user experience of users is further improved while the safety of the patient is ensured.

In an implementable solution, the preset low heart rate is greater than 0 bpm and less than or equal to 40 bpm, preferably, the preset low heart rate includes 10 bpm to 30 bpm, and further, the preset low heart rate may be set to 20 bpm. It should be noted that the pacing therapy mode of this embodiment is also applicable when the heart rate of the patient is 0 bpm, so as to pace and save the patient without heartbeat in time.

The time length of the preset low heart rate includes 1 s-5 min (i.e., 1 second to five minutes), the time length of the preset low heart rate duration can be adjusted and determined according to the physical states of different patients or other actual conditions, and any time length of the preset low heart rate which can be reasonably applied to the technical solutions of the present disclosure in the actual pacing process belongs to the protection scope of the present disclosure.

In addition, the time length of the preset low heart rate may also include 1 s to 60 s, preferably, the time length of the preset low heart rate is 1 s to 20 s, and further, the time length of the preset low heart rate may be set to 10 s.

The preset pacing frequency includes 35 bpm-90 bpm, the preset pacing frequency can be adjusted and determined according to the physical conditions of different patients or other actual conditions, and any preset pacing frequency which can be reasonably applied to the technical solutions of the present disclosure in the actual pacing process belongs to the protection scope of the present disclosure.

In addition, the preset pacing frequency may also include 40 bpm to 80 bpm, preferably, the preset pacing frequency is 50 bpm to 65 bpm. Further, the preset pacing frequency may be set to 60 bpm.

The step S203 is followed by the steps:

S204, detecting second response information of a ventricle of the patient to the preset pacing frequency under the pacing operation;

S205, judging whether an R wave has occurred in the second response information, and if so, executing step S206; if not, executing step S207;

S206, determining that preset pacing output is effective, and continuing to pace the patient using the preset pacing output; and S207, determining that the preset pacing output is ineffective, and adjusting the preset pacing output to pace the patient using the adjusted pacing output.

Alternatively, the step S203 is followed by the steps:

S208, performing a pacing-triggered cardiac contractility modulation on the patient, that is, when the patient is in a critical state (i.e., the patient is in severe bradycardia or cardiac arrest), performing cardiac pacing on the patient using the preset pacing frequency and the pacing output, and performing CCM modulation on the patient by pacing triggering so as to achieve the effect of restoring the heart rate of the patient to normal.

Alternatively, the step S203 is followed by the steps:

S209, detecting the second response information of the ventricle of the patient to the preset pacing output under the pacing operation, and determining that the preset pacing output is effective when the R wave has occurred in the second response information, and continuing to pace the patient using the preset pacing output, and simultaneously performing an R wave-triggered cardiac contractility modulation on the patient.

That is, when the patient is in a critical state, the patient is subjected to cardiac pacing using the preset pacing frequency and preset pacing output, which is triggered by pacing or is subjected to CCM modulation by pacing triggering or R wave triggering when the R wave is monitored to be present in the response information of the ventricle of the patient under cardiac pacing, that is, based on a processing scheme combining the pacing output, the detection of the R wave and the CCM cardiac contractility modulation, the treatment effect on the patient is greatly improved, and the timeliness and effectiveness of restoring the heartbeat of the patient to be normal are ensured. If the patient occasionally has his own heartbeat during pacing, the CCM modulation is triggered by sensing the R wave. Where in medical devices/instruments (e.g., WCDs) that can only indirectly provide pacing output for the myocardium, the CCM is provided indirectly to the myocardium via a first electrode pair (i.e., the electrode pair configured to provide the pacing output). In medical devices/instruments (e.g., MCS) that can directly provide pacing output to the myocardium, the CCM is provided by the first electrode pair or other electrode pairs in direct contact with the myocardium (wherein at least one electrode is in contact with the myocardium).

Specifically, the step S207 specifically includes:

increasing the current pacing output, and pacing the patient using the increased pacing output;

detecting the second response information of the ventricle of the patient to the current pacing output under the pacing operation; and judging whether the R wave has occurred in the second response information, and if not, re-executing the step of increasing the current pacing output, and pacing the patient using the increased pacing output; if so, pacing the patient using the increased current pacing output, and taking the current pacing output as initial pacing output which is output to the patient by the medical device.

In order to ensure that effective pacing is performed from the beginning, in the pacing therapy process, pacing output higher than the cardiac pacing threshold to a certain degree is used to carry out pacing therapy on the patient, the response of the ventricle to the pacing output is measured simultaneously, and when the occurrence situation of the R wave is captured in the response information, the pacing therapy on the patient is continued with the current pacing output; when the occurrence situation of the R wave is not captured in the response information, the amplitude (or pulse width) of the pacing output is increased after a certain time (interval time length is adjustable) from delivering the previous pacing output to perform the pacing therapy on the patient again, for example, the increased pacing output is delivered again after 200 ms from delivering the previous pacing output; if the R wave has occurred, the increased current pacing output is continued to be used for pacing, and otherwise, the amplitude of the pacing output is continued to be increased step by step until the pacing output can enable the R wave to be present in the pacing output result, so that the effect of pacing the patient to provide blood as soon as possible is achieved.

Where once a new pacing output which can be successfully used for pacing is acquired, the new pacing output is stored for future pacing, thereby achieving the effect of intelligent pacing.

Specifically, the effectiveness of the pacing output is determined by means of multi-beat detection in the pacing therapy phase, specifically:

acquiring the second response information of each ventricular pacing beat by beat under the current pacing output, and judging whether the R wave has occurred in the second response information of each ventricular pacing, and if so, determining that the preset pacing output is effective, and continuing to pace the patient using the preset pacing output;

if not, determining that the preset pacing output is ineffective, increasing the current pacing output at the current heartbeat time and pacing the patient using the current pacing output, and re-executing the step of acquiring the second response information of each ventricular pacing beat by beat until acquiring effective pacing output which enables the R wave to be present in the second response information of each ventricular pacing;

moreover, acquiring the second response information after each pacing beat by beat under the current pacing output, and judging whether the R wave has occurred in the second response information after each pacing, and if so, determining that the preset pacing output is effective, and continuing to pace the patient using the preset pacing output, and simultaneously performing the R wave-triggered cardiac contractility modulation on the patient;

or, under the current pacing output, judging whether the R wave has occurred in the second response information of the first ventricular pacing, and if so, determining that the preset pacing output is effective, and continuing to pace the patient using the preset pacing output; if not, pacing the patient using the increased pacing output after the set time length until acquiring the effective pacing output which enables the R wave to be present in the second response information of each ventricular pacing;

moreover, judging whether the R wave has occurred in the second response information after the first pacing under the current pacing output, and if so, determining that the preset pacing output is effective, and continuing to pace the patient using the preset pacing output, and simultaneously performing the R wave-triggered cardiac contractility modulation on the patient.

The pacing effect of the current pacing output on the patient is determined in time by a multi-beat detection mode, and the current pacing output is continued to be used for pacing when the pacing output is effective; when the pacing is determined to be ineffective, the pacing output is increased in time to achieve the effect of rescuing the patient in time, so that the accuracy of determining the effectiveness of the pacing output is improved, and the pacing rescue efficiency is improved.

In addition, when the preset pacing output is increased by more than a set number of times, and/or when the preset pacing output is adjusted for a longer time than a set time length, the patient is paced using a maximum set pacing output to ensure that the capture of the patient occurs at the highest level.

In fact, during actual pacing therapy, when no R wave appears when the pacing output is increased for the first time, the pacing output is increased for the second time to the maximum output state of a pacing device, that is, the amplitude and pulse width of the pulses are both the maximum values of an instrument pulse generator, to ensure that the capture of the patient occurs at the fastest and most likely level.

In this embodiment, it is no longer aiming at patients with bradycardia in the traditional sense, but taking patients life-threatening states with severe bradycardia or even cardiac arrest caused by basic or acute heart disease as the objects needing pacing support; pacing is performed on the patient using the pacing output of the cardiac pacing threshold only under the condition of necessary pacing, so that the effect of timely and effective pacing to support the life of the patient is achieved, and the pacing is stopped when the heart rate of the patient recovers to a certain extent; in daily use, the patient also achieves a great degree of avoiding unnecessary pacing and reducing the effect of pain caused by pacing stimulation, so that the acceptance, compliance, and use experience of users on the medical instruments are improved. Meanwhile, when the pacing output of the cardiac pacing threshold is used to pace the patient, whether the R wave has occurred in the response information of the ventricle of the patient under the pacing output of the cardiac pacing threshold is monitored in time so as to determine the effectiveness of the cardiac pacing threshold, and the pacing output is increased in time for pacing when the pacing output is ineffective until the pacing output can enable the R-wave to be present in the response information, so that the effect of pacing the patient to provide blood as soon as possible is achieved; maximum pacing output is used for pacing when the number or time length of pacing output adjustments exceeds a certain range to ensure as much as possible that the capture of the patient occurs at the highest possible level.

Embodiment 4

Figure 7:
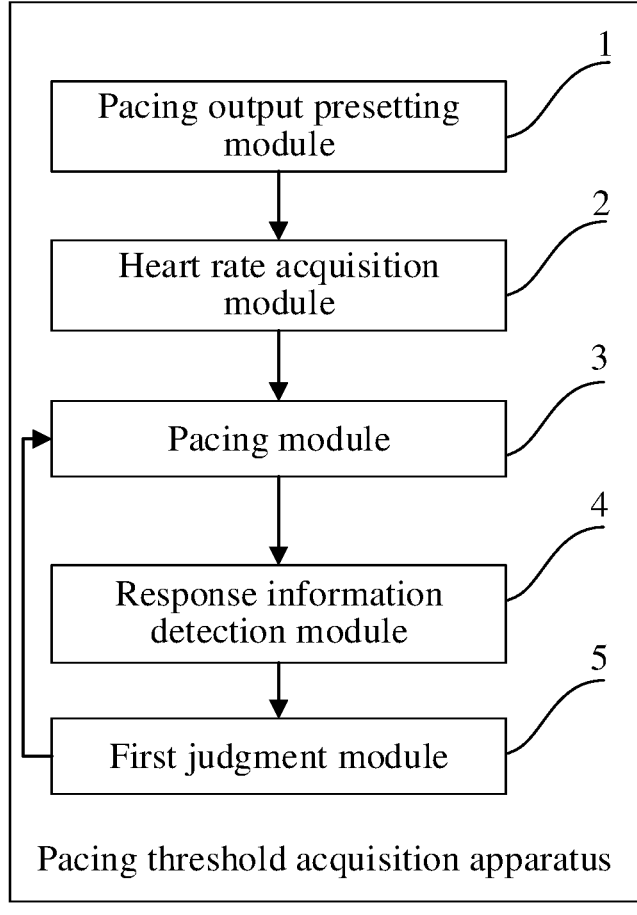
FIG. 7 is a module diagram of an acquisition apparatus for a cardiac pacing threshold according to Embodiment 4 of the present disclosure.

As shown in FIG. 7, an acquisition apparatus for a cardiac pacing threshold according to this embodiment includes a pacing output presetting module 1, a heart rate acquisition module 2, a pacing module 3, a response information detection module 4, and a first judgment module 5.

The pacing output presetting module 1 is configured to preset an initial pacing output; wherein the initial pacing output includes an initial pacing voltage amplitude and/or pulse width.

The heart rate acquisition module 2 is configured to detect a first actual heart rate of the heart of a patient in a pacing test phase.

The pacing module 3 is configured to determine an initial pacing frequency according to the first actual heart rate, and pace the patient using the initial pacing frequency and the initial pacing output, wherein the initial pacing frequency is greater than the first actual heart rate.

Where the pacing test phase may be a time period (e.g., two or three o'clock in the morning) during which the patient is in a deep sleep state, and the pacing device automatically triggers the pacing test to acquire the cardiac pacing threshold. It is certain that the pacing test phase may be reset and adjusted according to the work and rest time or usage habits of different patients.

The response information detection module 4 is configured to detect first response information of a ventricle of the patient to a current pacing output under a pacing operation;

wherein a ventricular response can be reflected by, but not limited to, a body surface, a subcutaneous, endocardial, epicardial electrocardiogram.

The first judgment module 5 is configured to adjust the current pacing output according to the occurrence situation of an R wave in the first response information to acquire the cardiac pacing threshold corresponding to the patient;

wherein when the heart rate state of the patient meets a pacing condition, preset pacing output which is output by the medical instrument/device is determined based on the cardiac pacing threshold, and the preset pacing output (pulse voltage amplitude and/or pulse width) is larger than the cardiac pacing threshold. Where if no cardiac pacing threshold exists at present, the pacing output preset by the medical instrument when leaving a factory or manually by a doctor is used.

The cardiac pacing threshold is a value determined according to different physical conditions of different patients, each patient is paced with pacing output adapted to the patient by acquiring the cardiac pacing threshold, so that the effect of customizing the output with the adaptive pacing output is achieved, and the rationality and effectiveness of pacing output setting are ensured.

In addition, the automatic pacing test can be performed on the patient regularly or irregularly over time based on the doctor's advice on the patient's use or the patient's usage habits and adaptability and the like to dynamically update the cardiac pacing threshold, so that the body and the state of illness of the patient can be tracked timely to obtain the pacing output adapted to the latest condition of the patient, which further ensures reasonable and effective pacing for the patient, further enhances the use experience of the patient; and simultaneously reduces the energy required for pacing, and extends the service time and lifespan of the instrument battery.

In this embodiment, by using the initial pacing output to pace the patient in the pacing test phase, whether the R wave has occurred in the response information corresponding to the ventricle of the patient is synchronously detected, and based on monitoring whether the R wave has occurred, pacing is performed using the pacing output that is adapted to each patient according to different physical conditions of different patients, and the output is customized with the adaptive pacing output, which ensures reasonable and effective pacing for different patients, and effectively improves the use experience of the patients.

Embodiment 5

Figure 8:
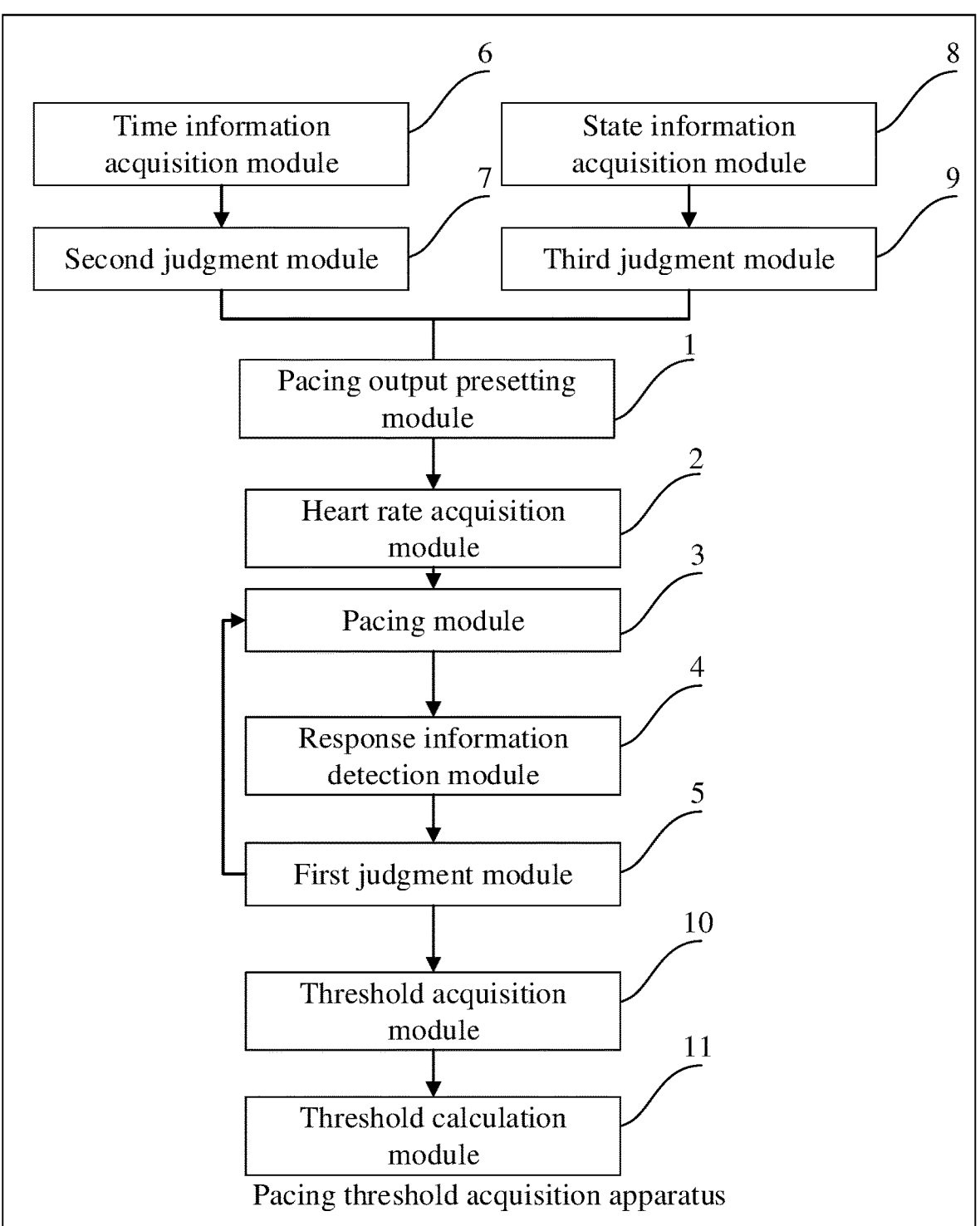
FIG. 8 is a module diagram of an acquisition apparatus for a cardiac pacing threshold according to Embodiment 5 of the present disclosure.

As shown in FIG. 8, an acquisition apparatus for a cardiac pacing threshold according to this embodiment is a further improvement on Embodiment 4.

The pacing module 3 is configured to deliver the initial pacing output to pace the patient using a first electrode pair disposed in the medical device.

The response information detection module 4 is configured to sense and obtain the first response information of the ventricle of the patient to the current pacing output using a second electrode pair disposed in the medical device;

wherein when the first electrode pair is a defibrillation electrode, the second electrode pair is a sensing electrode; alternatively, when the first electrode pair is a sensing electrode, a pacing electrode or a defibrillation electrode, the second electrode pair is a defibrillation electrode.

The acquisition apparatus for the cardiac pacing threshold according to this embodiment further includes a time information acquisition module 6 and a second judgment module 7.

The time information acquisition module 6 is configured to acquire current time information; and the second judgment module 7 is configured to judge whether the current time information is within a preset time period, and if so, determine to enter the pacing test phase.

That is, by setting a certain time (e.g., a certain time period of each day) as a pacing test time, once the set time is reached, the pacing device automatically enters the pacing test phase to automatically acquire the current cardiac pacing threshold corresponding to the patient.

Alternatively, the acquisition apparatus for the cardiac pacing threshold according to this embodiment further includes a state information acquisition module 8 and a third judgment module 9.

The state information acquisition module 8 is configured to acquire body state information of the patient; and the third judgment module 9 is configured to judge whether the patient is in a preset state according to the body state information, and if so, determine to enter the pacing test phase.

That is, when the patient is in the sleep state, such as the deep sleep at two or three o'clock in the morning, the pacing device automatically enters the pacing test phase, and automatically acquires the current cardiac pacing threshold corresponding to the patient without affecting the normal daily life or night sleep, avoiding uncomfortable experience of the patient and ensuring the comfort in use for the patient.

Of course, the pacing device may also be automatically triggered to enter the pacing test procedure according to other set conditions, as long as the cardiac pacing threshold can be acquired effectively in time, and therefore, the details are not repeated here.

When different pacing test phases are preset, the acquisition apparatus according to this embodiment further includes a threshold acquisition module 10 and a threshold calculation module 11.

The threshold acquisition module 10 is configured to acquire the cardiac pacing threshold obtained in each of the pacing test phases respectively; and the threshold calculation module 11 is configured to calculate and obtain a new cardiac pacing threshold according to a plurality of the cardiac pacing thresholds.

In particular, the threshold calculation module 11 is configured to perform statistical calculations based on the plurality of the cardiac pacing thresholds, including, but not limited to, an average calculation or a weighted average calculation, etc. to obtain a new cardiac pacing threshold.

Different cardiac pacing thresholds corresponding to the same patient in the same time period and/or different time periods are obtained by setting a plurality of pacing test phases, and then a final cardiac pacing threshold is obtained by comprehensively calculating the plurality of the cardiac pacing thresholds, that is, the accuracy of the cardiac pacing threshold is further ensured by combining a plurality of groups of data.

The first judgment module is configured to judge whether the R wave has occurred in the first response information, and if so, decrease the current pacing output, and call the pacing module to pace the patient using the decreased pacing output;

the response information detection module is configured to detect the first response information of the ventricle of the patient to the current pacing output under the pacing operation;

the first judgment module is configured to decrease the current pacing output again when the R wave has occurred in the first response information, and call the pacing module to pace the patient using the decreased pacing output; and the first judgment module is further configured to take previous pacing output as the cardiac pacing threshold corresponding to the patient when no R wave has occurred in the first response information but the R wave has occurred in the previous pacing output.

That is, if the R wave has occurred in the response of the current pacing output acting on the ventricle of the patient, it indicates that the current pacing output can effectively pace the patient and that a case of being too high may exist, at this time, the patient is paced again by decreasing the pacing output step by step, and if the R wave continues to be present in the response of the ventricle of the patient, the pacing output continues to be decreased until no R wave has occurred in the response of the ventricle of the patient, and then it indicates that the current pacing output is too low, and the previous adjusted pacing output is determined to be the cardiac pacing threshold corresponding to the patient.

Where the pacing output can be further refined and adjusted between the current pacing output and the previous pacing output to obtain a more accurate cardiac pacing threshold, specifically, how to refine and adjust it can be preset, and certainly, the refining and adjusting mode can also be reset and adjusted according to actual requirements.

In addition, in order to acquire the cardiac pacing threshold more matched with the patient, the adjusting mode of the pacing output can be further optimized, for example, the amplitude of two adjacent pacing outputs is adjusted in a mode of decreasing by a large span first and then decreasing by a small span, so that the speed and the accuracy of acquiring the cardiac pacing threshold are ensured; or the amplitude of two adjacent pacing outputs is adjusted in a mode of decreasing by the small span all the time, so that the accuracy of the cardiac pacing threshold is effectively ensured. It is certain that technical solutions based on other adjusting modes of pacing output may also be used, as long as the cardiac pacing threshold corresponding to the patient can be finally obtained, and therefore, the details are not described herein.

Alternatively, the first judgment module is configured to judge whether the R wave has occurred in the first response information, and if not, increase the current pacing output, and call the pacing module to pace the patient using the increased pacing output;

the response information detection module is configured to detect the first response information of the ventricle of the patient to the current pacing output under the pacing operation;

the first judgment module is further configured to increase the current pacing output again when no R wave has occurred in the first response information, and call the pacing module to pace the patient using the increased pacing output; and the first judgment module is further configured to take the current pacing output as the cardiac pacing threshold corresponding to the patient when the R wave has occurred in the first response information.

That is, if no R wave has occurred in the response of the current pacing output acting on the ventricle of the patient, it indicates that the current pacing output cannot perform effective pacing on the patient, at this time, the patient is paced again by increasing the pacing output step by step, and if no R wave continues to be present in the response of the ventricle of the patient, the pacing output continues to be increased until the R wave has occurred in the response of the ventricle of the patient, and then it indicates that the current pacing output is too low, and the previous adjusted pacing output is determined to be the cardiac pacing threshold corresponding to the patient.

Where the pacing output can be further refined and adjusted between the current pacing output and the previous pacing output to obtain a more accurate cardiac pacing threshold, specifically, how to refine and adjust it can be preset, and certainly, the refining and adjusting mode can also be reset and adjusted according to actual requirements.

In addition, in order to acquire the cardiac pacing threshold more matched with the patient, the adjusting mode of the pacing output can be further optimized, for example, the amplitude of two adjacent pacing outputs is adjusted in a mode of increasing by a large span first and then increasing by a small span, so that the speed and the accuracy of acquiring the cardiac pacing threshold are ensured; or the amplitude of two adjacent pacing outputs is adjusted in a mode of increasing by the small span all the time, so that the accuracy of the cardiac pacing threshold is effectively ensured. It is certain that technical solutions based on other adjusting modes of pacing output may also be used, as long as the cardiac pacing threshold corresponding to the patient can be finally obtained, and therefore, the details are not described herein.

In an optional technical solution, a multi-beat monitoring approach is adopted to reasonably determine the cardiac pacing threshold that is really adapted to the patient, and the specific processing procedure is as follows:

when the R wave has occurred in the first response information detected after the current pacing output is decreased, the acquisition method includes:

acquiring the first response information of a second set number of ventricular pacing beat by beat after skipping the first response information of a first set number of ventricular pacing under the current pacing output;

determining that the current pacing output is ineffective when no R wave has occurred in the first response information of the ventricular pacing greater than a third set number, and increasing the current pacing output to pace the patient again, and then re-executing the step of acquiring the first response information of the second set number of ventricular pacing beat by beat after skipping the first response information of the first set number of ventricular pacing under the current pacing output, wherein the third set number is smaller than or equal to the second set number;

determining that the current pacing output is effective when the R wave has occurred in the first response information of the ventricular pacing greater than a fourth set number, simultaneously decreasing the current pacing output, pacing the patient using the decreased pacing output, and re-executing the step of acquiring the first response information of the second set number of the ventricular pacing beat by beat after skipping the first response information of the first set number of the ventricular pacing until the R wave has occurred in the first response information of the ventricular pacing smaller than or equal to the third set number, and then determining that the current pacing output is ineffective, and determining that the previous pacing output is effective, and taking the pulse voltage amplitude and/or pulse width of the previous pacing output as the cardiac pacing threshold, wherein the fourth set number is smaller than or equal to the second set number; and otherwise, continuing to acquire the first response information of the second set number of ventricular pacing beat by beat and analyzing the occurrence situation of the R wave until the cardiac pacing threshold is acquired.

For example, after a certain pacing output is output, the response condition corresponding to the first three beats is firstly ignored, then the response condition of the 4th to 6th beats is directly judged, and when the response information of the 4th to 6th beats indicates that the R wave has occurred in each beat, the current pacing output is determined to be effective; when the response information of the 4th to 6th beats indicates that no R wave has occurred in the three beats, the current pacing output is determined to be ineffective; otherwise, the response condition corresponding to the three beats from the current beat is continuously acquired and analyzed, wherein the specific analysis process is the same as the above process, and therefore the detailed description is omitted. It is certain that the multi-beat detection mode can be adjusted according to actual situations.

In this embodiment, the initial pacing output and the initial pacing output are used for pacing the patient in the pacing test phase, whether the R wave has occurred in response information corresponding to the ventricle of the patient is synchronously detected through the second electrode pair, and the pacing output is continuously increased when no R wave has occurred or the pacing output is continuously decreased when the R wave has occurred until the pacing output (the cardiac pacing threshold) which just can trigger the R wave to be present is obtained, so that based on monitoring whether the R wave has occurred, pacing is performed using the pacing output adapted to each patient according to different physical conditions of different patients, the output is customized with the adaptive pacing output, so that reasonable and effective pacing for different patients is ensured, and the use experience of the patients is effectively improved, and the problem of patients when pacing is not captured is decreased; in addition, the cardiac pacing threshold is dynamically updated, so that reasonable and effective pacing for the patients is further ensured, and the use experience of the patients is further improved.

Embodiment 6

The cardiac pacing threshold in the pacing control apparatus according to this embodiment may be determined based on an existing acquisition mode in the prior art, or may be obtained by using an acquisition mode corresponding to the above cardiac pacing threshold acquisition apparatus in the present disclosure, and specifically may be selected or adjusted according to an actual scene.

Figure 9:
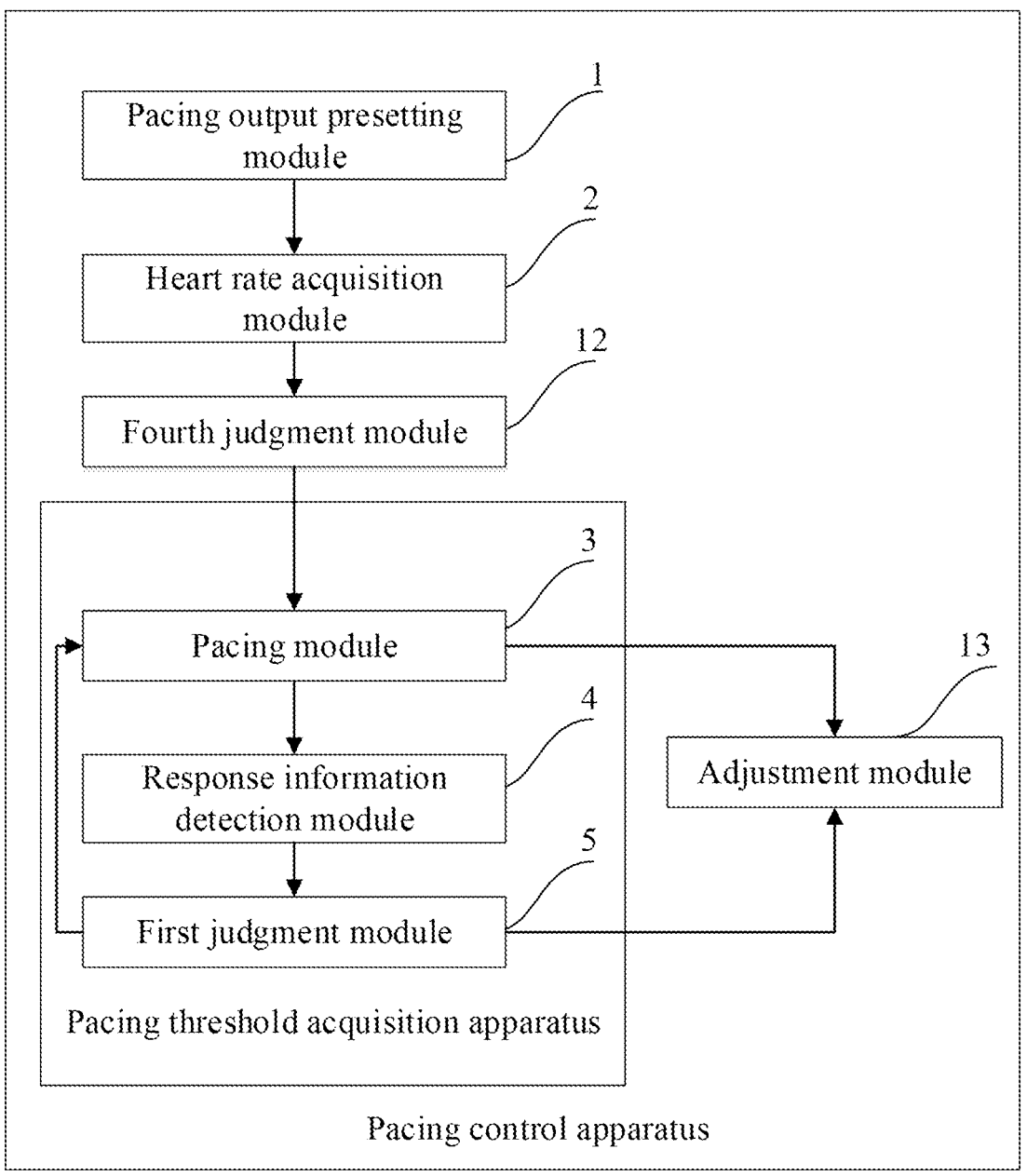
FIG. 9 is a module diagram of a pacing control apparatus according to Embodiment 6 of the present disclosure.

As shown in FIG. 9, the pacing control apparatus according to this embodiment further includes a heart rate acquisition module 2 and a fourth judgment module 12.

The heart rate acquisition module 2 is configured to acquire a second actual heart rate of the heart of a patient; and the fourth judgment module 12 is configured to judge whether the second actual heart rate meets a preset low heart rate condition, and if so, call a pacing module 3 to perform cardiac pacing on a patient using a preset pacing frequency of the cardiac pacing threshold; wherein the preset low heart rate condition is used for representing that the patient is in a life-threatening state;

It is not only used for patients suffering from bradycardia in the traditional sense, but also used for patients suffering from severe bradycardia or even cardiac arrest, and patients in the foregoing life-threatening states are taken as objects needing pacing support, who are likely to die without pacing (patients in urgent need of assistance), that is, the pacing operation in the present disclosure is only implemented in a "last resort"/"life-saving" situation.

Specifically, the triggering condition for implementing the pacing operation is preset, so that the patient is paced using higher pacing output only under the condition of necessary pacing, and the effect of timely and effectively pacing to support the life of the patient is achieved; meanwhile, in daily use, the patient also achieves a great degree of avoiding unnecessary (non-life saving) pacing and the effect of pain caused by pacing stimulation, particularly, occasional bradycardia or transient stop and jump cannot be triggered to pace, and the acceptance, compliance and use experience of users on the medical instruments are improved.

Specifically, the fourth judgment module 12 is configured to determine whether the second actual heart rate is smaller than a preset low heart rate, and if so, call the pacing module 3 to perform cardiac pacing on the patient using the preset pacing frequency.

By monitoring the real-time heart rate of the patient, when the real-time heart rate is smaller than the preset low heart rate (far smaller than the preset low limit heart rate in the existing pacing control mode), the condition that the patient is in urgent need of assistance is determined, that is, the cardiac pacing for the patient is triggered only when the heart rate of the patient is very low, and the effect of timely and effective pacing to support the life of the patient is achieved.

Alternatively, the pacing control apparatus according to this embodiment further includes a time length acquisition module.

The fourth judgment module 12 is configured to judge whether the second actual heart rate is smaller than the preset low heart rate, and if so, call the time length acquisition module to acquire duration of a first low heart rate when the heart of the patient is at the second actual heart rate.

The fourth judgment module 12 is further configured to call the pacing module 3 to perform cardiac pacing on the patient using the preset pacing frequency and the pacing output when the duration of the first low heart rate reaches the time length of the preset low heart rate.

Real-time monitoring of real-time heart rate of the patient triggers pacing only when the second actual heart rate is less than the preset low heart rate and the duration of the first low heart rate of the second actual heart rate reaches or exceeds the time length of the preset low heart rate, avoiding the occurrence of unnecessary pacing operations caused by the heart rate of the patient accidentally falling below the preset low heart rate, so that better pacing monitoring function is achieved, and the use experience of users is further improved while the safety of the patient is ensured.

In an implementable solution, the preset low heart rate is greater than 0 bpm and less than or equal to 40 bpm, and the preset low heart rate is far lower than the preset low limit heart rate in the existing pacing control mode. Preferably, the preset low heart rate includes 10 bpm to 30 bpm, and further, the preset low heart rate may be set to 20 bpm.

The time length of the preset low heart rate includes 1 s-5 min (i.e., 1 second to five minutes), the time length of the preset low heart rate duration can be adjusted and determined according to the physical states of different patients or other actual conditions, and any time length of the preset low heart rate which can be reasonably applied to the technical solutions of the present disclosure in the actual pacing process belongs to the protection scope of the present disclosure.

The time length of the preset low heart rate includes 1 s-60 s, preferably, the time length of the preset low heart rate is 1 s-20 s, and further, the time length of the preset low heart rate may be set to 10 s.

The preset pacing frequency includes 35 bpm-90 bpm, the preset pacing frequency can be adjusted and determined according to the physical conditions of different patients or other actual conditions, and any preset pacing frequency which can be reasonably applied to the technical solutions of the present disclosure in the actual pacing process belongs to the protection scope of the present disclosure.

In addition, the preset pacing frequency may also include 40 bpm to 80 bpm, preferably, the preset pacing frequency is 50 bpm to 65 bpm. Further, the preset pacing frequency may be set to 60 bpm.

The preset pacing frequency, the preset low heart rate and the time length of the preset low heart rate in this embodiment are all parameters which can be reset according to the specific conditions of different patients. Considering different patients have certain differences in physical states, in order to enable each patient to obtain a specific pacing therapy, the preset low heart rate, the time length of the preset low heart rate and the preset pacing frequency which are adapted to each patient and used for triggering pacing are finally determined by comprehensively considering multiple parameters such as the medical history, the current illness state, the medicine use condition, and the pacing use requirement of each patient in advance, so that the safety of the patient is guaranteed, and the experience of the patients is guaranteed to the maximum extent.

The response information detection module 4 is configured to detect second response information (an electrocardiographic signal sensed by a second electrode pair) of a ventricle of the patient to preset pacing output under the pacing operation;

the first judgment module 5 is configured to judge whether an R wave has occurred in the second response information, and if so, determine the preset pacing output to be effective, and continue to call the pacing module 3 to pace the patient using the preset pacing output; otherwise, it is configured to determine the preset pacing output to be ineffective, and call the pacing module 3 to adjust the preset pacing output to pace the patient using the adjusted pacing output.

Alternatively, the adjustment module 13 is configured to perform a pacing-triggered cardiac contractility modulation (CCM) on the patient, that is, when the patient is in a critical state, CCM stimulation is directly performed on the patient to achieve the effect of enabling the heartbeat of the patient to be restored to be normal.

Alternatively, the response information detection module 4 is configured to detect second response information of the ventricle of the patient to the preset pacing output under the pacing operation, and the first judgment module 5 is configured to judge whether the R wave has occurred in the second response information, and if so, call the adjustment module to perform R wave-triggered myocardial contractility modulation on the patient, and meanwhile, continue to call the pacing module to pace the patient using the preset pacing output due to the fact that the preset pacing output is effective.

That is, when the patient is in a critical state, the patient is subjected to cardiac pacing using the preset pacing frequency and preset pacing output, which is triggered by pacing, or is subjected to CCM regulation by pacing triggering or R wave triggering when the R wave has occurred in the response information of the ventricle of the patient under cardiac pacing, that is, based on a processing scheme combining the pacing output, the detection of the R wave and the CCM cardiac contractility modulation, the treatment effect on the patient is greatly improved, and the timeliness and the effectiveness of restoring the heartbeat of the patient to normal are ensured. If the patient occasionally has his own heartbeat during pacing, the CCM modulation is triggered by sensing the R wave.

Specifically, the pacing module 3 is configured to increase the current pacing output, and pace the patient using the increased pacing output.

The response information detection module 4 is configured to detect the second response information of the ventricle of the patient to the preset pacing output under the pacing operation.

The pacing module 3 is further configured to increase the current pacing output again when no R wave has occurred in the second response information, and pace the patient using the increased pacing output.

The pacing module 3 is further configured to pace the patient using the increased current pacing output when the R wave has occurred in the second response information, and take the current pacing output as initial pacing output which is output by the medical device to the patient.

In order to ensure that effective pacing is performed from the beginning, in the pacing therapy process, pacing output higher than the cardiac pacing threshold to a certain degree is used to carry out pacing therapy on the patient, meanwhile, the response of the ventricle to the pacing output is measured simultaneously, and when the occurrence situation of the R wave is captured in the response information, the pacing therapy on the patient is continued with the current pacing output; when the occurrence situation of the R wave is not captured in the response information, the amplitude (or pulse width) of the pacing output is increased after a certain time (interval time length is adjustable) from delivering the previous pacing output to carry out pacing therapy on the patient again, for example, the increased pacing output is delivered again after 200 ms (the time is adjustable) from delivering the previous pacing output; if the R wave has occurred, the increased current pacing output is continued to be used for pacing, and otherwise, the amplitude of the pacing output is continued to be increased step by step until the pacing output can enable the R wave to be present in the pacing output result, so that the effect of pacing the patient to provide blood as soon as possible is achieved.

Where once a new pacing output which can be successfully used for pacing is acquired, the new pacing output is stored for future pacing, thereby achieving the effect of intelligent pacing.

In addition, the pacing module 3 is further configured to pace the patient using maximum set pacing output when the number of times of increasing the preset pacing output is greater than a set number of times, and/or a time length of adjusting the preset pacing output exceeds a set time length.

In fact, during actual pacing therapy, when no R wave appears when the pacing output is increased for the first time, the pacing output is increased for the second time to the maximum output state of a pacing device, that is, the amplitude and pulse width of the pulses are both the maximum values of an instrument pulse generator, to ensure that the capture of the patient occurs at the fastest and most likely level.

In this embodiment, it is no longer aiming at patients with bradycardia in the traditional sense, but taking patients life-threatening states with severe bradycardia or even cardiac arrest caused by basic or acute heart disease as the objects needing pacing support; pacing is performed on the patient using the pacing output of the cardiac pacing threshold only under the condition of necessary pacing, so that the effect of timely and effective pacing to support the life of the patient is achieved, and the pacing is stopped when the heart rate of the patient recovers to a certain extent; in daily use, the patient also achieves a great degree of avoiding unnecessary pacing and reducing the effect of pain caused by pacing stimulation, so that the acceptance, compliance, and use experience of users on the medical instruments are improved.

When the pacing output higher than the cardiac pacing threshold to a certain extent is used to pace the patient, whether the R wave has occurred in the response information of the ventricle of the patient under the pacing output of the cardiac pacing threshold is monitored in time so as to determine the effectiveness of the cardiac pacing output, and the pacing output is increased in time for pacing when the pacing output is ineffective until the pacing output can enable the R wave to be present in the response information, so that the effect of pacing the patient to provide blood as soon as possible is achieved; maximum pacing output is used for pacing when the number or time length of pacing output adjustments exceeds a certain range to ensure as much as possible that the capture of the patient occurs at the highest possible level.

Embodiment 7

The medical device according to this embodiment includes the pacing control apparatus according to Embodiment 6.

Where the medical device includes but is not limited to a wearable cardioverter defibrillator (WCD), an external defibrillator (e.g., an AED), an external temporary pacemaker, a subcutaneous implantable cardioverter defibrillator SICD or a mechanical circulation support device MCS.

Specifically, the pacing therapy described above may be applied in the following aspects, which can not only provide pacing therapy, but also provide the efficiency and adaptability of the pacing therapy at the same time.

The incorporation of the pacing therapy into wearable, extracorporeal, and non-cardiac direct contact defibrillation systems, such as wearable defibrillation systems (WCDs) and subcutaneous defibrillation systems (SICDs), can provide the pacing therapy in the event of severe bradycardia or cardiac arrest, thus saving the life of a patient. Also for example, AEDs and the like rescue patients outside or inside the hospital; they can also provide the pacing therapy in public places or in external defibrillators for hospitals or ambulances, saving patients from severe bradycardia or cardiac arrest. For SICDs, the approach of pacing threshold management may still be implemented if the pacing function is through other separate instruments, such as a leadless pacemaker implanted in a ventricle. One approach is that a first electrode pair is a pacing electrode pair on the leadless pacemaker and a second electrode pair is a defibrillation electrode (or sensing electrode) of the SICD. The function can be achieved by using the functional blocks of the present disclosure, but the information of the existence of an R wave, pacing output changes and the like is transmitted by the wireless communication function between the SICD and the leadless pacemaker to determine the threshold.

The pacing therapy combined with acute (or short-term) and long-term (or chronic) MCS devices (e.g., LVADs) is used for the treatment of bradycardia or cardiac arrest.

This can also be used to expand the application range of current external temporary pacemakers (with or without defibrillation function) in addition to venous or epicardial pacing, and provide transcutaneous pacing. This would make it possible to more widely use emergency ("life-saving") pacing when "time is critical" and/or "no experienced physicians can place temporary pacing leads through veins". This may, for example, expand the use of temporary pacing in small, community or rural hospitals to provide timely assistance for patients with severe bradycardia (e.g., third degree bradycardia) or cardiac arrest, particularly syncope. The pacing function here may be triggered automatically (as described above) or manually.

By adding the pacing therapy to the above instruments, it is also possible to carry out ATP therapy when necessary for patients with severe heart failure who experience persistent ventricular arrhythmias.

The medical device in this embodiment uses the pacing control apparatus described above, can pace the patient using the pacing output adapted to each patient, and customize the output with the adaptive pacing output, so that the reasonable and effective pacing for different patients is ensured; it can dynamically update the cardiac pacing threshold to pace the patient with more reasonable pacing output; for a patient in a life-threatening state with severe bradycardia or even cardiac arrest, the patient is paced only under the condition of necessary pacing, so that the effect of timely and effective pacing to support the life of the patient is achieved; in addition, whether the R wave has occurred in response information of a ventricle of the patient under pacing is monitored in time to determine the effectiveness of cardiac pacing, then the pacing output is adjusted in time when ineffective to ensure that the patient is paced as soon as possible to provide blood circulation, and the pacing effect on the patient and the use experience of the patient are greatly improved. Moreover, CCM modulation is provided under pacing or R wave triggering to better restore/support systolic function.

Although the specific embodiments of the present disclosure have been described above, it should be understood by those skilled in the art that these are merely illustrative examples and that a variety of changes or modifications can be made to these embodiments without departing from the principles and essence of the present disclosure. Therefore, the scope of protection of the present disclosure is limited by the appended claims.

What is claimed is:

1. A medical device, wherein the medical device comprises a pacing control apparatus, and the pacing control apparatus comprises an acquisition apparatus for a cardiac pacing threshold;

the acquisition apparatus comprises:

a pacing output presetting module, configured to preset an initial pacing output; wherein the initial pacing output comprises an initial pacing voltage amplitude and/or pulse width;

a heart rate acquisition module, configured to detect a first actual heart rate of the heart of a patient in a pacing test phase;

a pacing module determining an initial pacing frequency according to the first actual heart rate, and pacing the patient using the initial pacing frequency and the initial pacing output, wherein the initial pacing frequency is greater than the first actual heart rate;

a response information detection module, configured to detect first response information of a ventricle of the patient to a current pacing output under a pacing operation;

the response information detection module is also configured to acquire the first response information of a second set number of ventricular pacing beat by beat after skipping the first response information of a first set number of ventricular pacing under the current pacing output;

a first judgment module, configured to adjust the current pacing output according to the occurrence situation of an R wave in the first response information of each of the second set number of ventricular pacing to acquire a cardiac pacing threshold corresponding to the patient;

wherein when the heart rate state of the patient meets a pacing condition, a preset pacing output which is output by the medical device is determined based on the cardiac pacing threshold, and the preset pacing output is greater than the cardiac pacing threshold.

2. The medical device according to claim 1, wherein the pacing control apparatus further comprises:

the heart rate acquisition module, configured to acquire a second actual heart rate of the heart of a patient;

a fourth judgment module, configured to judge whether the second actual heart rate meets a preset low heart rate condition, and if so, perform cardiac pacing on the patient using a preset pacing frequency and a preset pacing output; wherein the preset low heart rate condition is used for representing that the patient is in a life-threatening state; and a response information detection module, configured to detect second response information of a ventricle of the patient to the preset pacing output under a pacing operation; a first judgment module, configured to judge whether an R wave has occurred in the second response information, and if so, determine that the preset pacing output is effective, and continue to call a pacing module to pace the patient using the preset pacing output: otherwise, determine that the preset pacing output is ineffective, and adjust the preset pacing output to call the pacing module to pace the patient using the adjusted pacing output; or, an adjustment module, configured to perform a pacing-triggered cardiac contractility modulation on the patient; or, the response information detection module is configured to detect the second response information of the ventricle of the patient to the preset pacing output under the pacing operation; the first judgment module is configured to judge whether the R wave has occurred in the second response information, and if so, determine that the preset pacing output is effective, and continue to call the pacing module to pace the patient using the preset pacing output, and call the adjustment module to perform an R wave-triggered cardiac contractility modulation on the patient.

3. The medical device according to claim 2, wherein the pacing control apparatus is integrated in the medical device.

4. The medical device according to claim 3, wherein the medical device comprises a wearable cardioverter defibrillator WCD, an external defibrillator, an external temporary pacemaker, an implantable cardioverter defibrillator ICD, a subcutaneous implantable cardioverter defibrillator S-ICD, or a mechanical circulatory support device MCS.

5. An acquisition method for a cardiac pacing threshold, comprising:

presetting an initial pacing output; wherein the initial pacing output comprises an initial pacing voltage amplitude and/or pulse width;

detecting a first actual heart rate of the heart of a patient in a pacing test phase;

determining an initial pacing frequency according to the first actual heart rate, and pacing the patient using the initial pacing frequency and the initial pacing output, wherein the initial pacing frequency is greater than the first actual heart rate;

detecting first response information of a ventricle of the patient to a current pacing output under a pacing operation;

acquiring the first response information of a second set number of ventricular pacing beat by beat after skipping the first response information of a first set number of ventricular pacing under the current pacing output;

analyzing occurrence situation of an R wave in the first response information of each of the second set number of ventricular pacing; and adjusting the current pacing output according to the occurrence situation of an R wave in the first response information of each of the second set number of ventricular pacing to acquire a cardiac pacing threshold corresponding to the patient;

wherein when the heart rate of the patient meets a pacing condition, a preset pacing output which is output by a medical device is determined based on the cardiac pacing threshold, and the preset pacing output is greater than the cardiac pacing threshold.

6. The acquisition method for the cardiac pacing threshold according to claim 5, wherein the step of adjusting the current pacing output according to the occurrence situation of the R wave in the first response information of each of the second set number of ventricular pacing to acquire the cardiac pacing threshold corresponding to the patient comprises:

judging whether the R wave has occurred in the first response information, and if so, decreasing the current pacing output, and pacing the patient using the decreased pacing output;

detecting the first response information of the ventricle of the patient to the current pacing output under the pacing operation; and re-executing the step of decreasing the current pacing output when the R wave has occurred in the first response information until no R wave has occurred in the first response information and then taking a previous pacing output as the cardiac pacing threshold corresponding to the patient.

7. The acquisition method for the cardiac pacing threshold according to claim 5, wherein the step of adjusting the current pacing output according to the occurrence situation of the R wave in the first response information of each of the second set number of ventricular pacing to acquire the cardiac pacing threshold corresponding to the patient comprises:

judging whether the R wave has occurred in the first response information, and if not, increasing the current pacing output, and pacing the patient using the increased pacing output;

detecting the first response information of the ventricle of the patient to the current pacing output under the pacing operation; and re-executing the step of increasing the current pacing output when no R wave has occurred in the first response information until the R wave has occurred in the first response information, and then taking the current pacing output as the cardiac pacing threshold corresponding to the patient.

8. The acquisition method for the cardiac pacing threshold according to claim 7, wherein when the R wave has occurred in the first response information, the acquisition method comprises:

determining that the current pacing output is ineffective when no R wave has occurred in the first response information of the ventricular pacing greater than a third set number, and increasing the current pacing output to pace the patient again, and then re-executing the step of acquiring the first response information of the second set number of ventricular pacing beat by beat after continuing to skip the first response information of the first set number of ventricular pacing under the current pacing output, wherein the third set number is smaller than the second set number.

9. The acquisition method for the cardiac pacing threshold according to claim 8, wherein the acquisition method further comprises:

determining that the current pacing output is effective when the R wave has occurred in the first response information of the ventricular pacing greater than a fourth set number, simultaneously decreasing the current pacing output, pacing the patient using the decreased pacing output, and re-executing the step of acquiring the first response information of the second set number of ventricular pacing beat by beat after skipping the first response information of the first set number of ventricular pacing until the R wave has occurred in the first response information of the ventricular pacing smaller than or equal to the third set number, and then determining that the current pacing output is ineffective, and determining that the previous pacing is effective, and taking a pulse voltage amplitude and/or pulse width of the previous pacing as the cardiac pacing threshold, wherein the fourth set number is smaller than the second set number; and otherwise, continuing to acquire the first response information of the second set number of ventricular pacing beat by beat and analyzing the occurrence situation of the R wave until the cardiac pacing threshold is acquired.

10. The acquisition method for the cardiac pacing threshold according to claim 5, wherein the step of pacing the patient using the initial pacing output comprises:

delivering the initial pacing output using a first electrode pair disposed in the medical device to pace the patient;

the step of detecting the first response information of the ventricle of the patient to the current pacing output under the pacing operation comprises:

sensing to obtain the first response information of the ventricle of the patient to the current pacing output using a second electrode pair disposed in the medical device;

wherein when the first electrode pair is a defibrillation electrode, the second electrode pair is a sensing electrode; or, when the first electrode pair is a sensing electrode, a pacing electrode or a defibrillation electrode, the second electrode pair is a defibrillation electrode.

11. The acquisition method for the cardiac pacing threshold according to claim 10, wherein when the first electrode pair is the defibrillation electrode, the first electrode pair is configured to be placed on the skin of the patient to pace the patient.

12. The acquisition method for the cardiac pacing threshold according to claim 5, wherein when different pacing test phases are preset, the acquisition method further comprises:

acquiring the cardiac pacing threshold obtained in each of the pacing test phases respectively; and performing an average calculation or a weighted average calculation based on a plurality of the cardiac pacing thresholds to obtain a new cardiac pacing threshold.

13. The acquisition method for the cardiac pacing threshold according to claim 5, wherein before the step of pacing the patient using the initial pacing frequency and the initial pacing output, the method further comprises:

acquiring current time information, judging whether the current time information is within a preset time period, and if so, determining to enter the pacing test phase; and/or acquiring body state information of the patient, judging whether the patient is in a preset state according to the body state information, and if so, determining to enter the pacing test phase.

14. A pacing control method, comprising:

acquiring a second actual heart rate of the heart of a patient;

judging whether the second actual heart rate meets a preset low heart rate condition, and if so, performing cardiac pacing on the patient using a preset pacing frequency and a preset pacing output: wherein the preset low heart rate condition is used for representing that the patient is in a life-threatening state; and detecting second response information of a ventricle of the patient to the preset pacing output under a pacing operation, acquiring the second response information of a second set number of ventricular pacing beat by beat after skipping the second response information of a first set number of ventricular pacing under the preset pacing output, judging whether an R wave has occurred in the second response information of each of the second set number of ventricular pacing, and if so, determining that the preset pacing output is effective, and continuing to pace the patient using the preset pacing output; otherwise, determining that the preset pacing output is ineffective, and adjusting the preset pacing output to pace the patient using the adjusted pacing output; or, performing a pacing-triggered cardiac contractility modulation on the patient; or, detecting the second response information of the ventricle of the patient to the preset pacing output under the pacing operation, acquiring the second response information of a second set number of ventricular pacing beat by beat after skipping the second response information of a first set number of ventricular pacing under the preset pacing output, judging whether the R wave has occurred in the second response information of each of the second set number of ventricular pacing, and if so, determining that the preset pacing output is effective, and continuing to pace the patient using the preset pacing output, and simultaneously performing an R wave-triggered cardiac contractility modulation on the patient.

15. The pacing control method according to claim 14, wherein the step of adjusting the preset pacing output to pace the patient using the adjusted pacing output comprises:

increasing a current pacing output, and pacing the patient using the increased pacing output;

detecting the second response information of the ventricle of the patient to the current pacing output under the pacing operation; and re-executing the step of increasing the current pacing output when no R wave has occurred in the second response information until the R wave has occurred in the second response information, and then pacing the patient using the increased current pacing output, and taking the current pacing output as the cardiac pacing threshold corresponding to the patient.

16. The pacing control method according to claim 14, wherein the pacing control method further comprises:

pacing the patient using a maximum pacing output of a medical device when the number of times of increasing the preset pacing output is greater than a set number of times, and/or a time length of adjusting the preset pacing output exceeds a set time length.

17. The pacing control method according to claim 14, wherein the step of judging whether the R wave has occurred in the second response information of each of the second set number of ventricular pacing, if so, determining that the preset pacing output is effective, and continuing to pace the patient using the preset pacing output; otherwise, determining that the preset pacing output is ineffective, and adjusting the preset pacing output to pace the patient using the adjusted pacing output comprises:

acquiring the second response information after each pacing beat by beat under the current pacing output, and judging whether the R wave has occurred in the second response information after each pacing, and if so, determining that the preset pacing output is effective, and continuing to pace the patient using the preset pacing output; and if not, determining that the preset pacing output is ineffective, increasing the current pacing output at a current pacing moment and pacing the patient using the increased pacing output, and continuing to execute the step of acquiring the second response information of each pacing output beat by beat until acquiring an effective pacing output which enables the R wave to be present in the second response information of each pacing output.

18. The pacing control method according to claim 14, wherein the step of judging whether the R wave has occurred in the second response information of each of the second set number of ventricular pacing, if so, determining that the preset pacing output is effective, and continuing to pace the patient using the preset pacing output; otherwise, determining that the preset pacing output is ineffective, and adjusting the preset pacing output to pace the patient using the adjusted pacing output comprises:

judging whether the R wave has occurred in the second response information after a first pacing under the current pacing output, and if so, determining that the preset pacing output is effective, and continuing to pace the patient using the preset pacing output; if not, pacing the patient using the increased pacing output after the set time length until acquiring the effective pacing output which enables the R wave to be present in the second response information of each pacing.

19. The acquisition method for the cardiac pacing threshold according to claim 14, wherein the acquisition method further comprises:

the step of detecting the second response information of the ventricle of the patient to the preset pacing output under the pacing operation, judging whether the R wave has occurred in the second response information, and if so, determining that the preset pacing output is effective, and continuing to pace the patient using the preset pacing output, and simultaneously performing the R wave-triggered cardiac contractility modulation on the patient comprises:

acquiring the second response information after each pacing beat by beat under the current pacing output, and judging whether the R wave has occurred in the second response information after each pacing, and if so, determining that the preset pacing output is effective, and continuing to pace the patient using the preset pacing output, and simultaneously performing the R wave-triggered cardiac contractility modulation on the patient.

20. The acquisition method for the cardiac pacing threshold according to claim 14, wherein the acquisition method further comprises:

the step of detecting the second response information of the ventricle of the patient to the preset pacing output under the pacing operation, judging whether the R wave has occurred in the second response information, and if so, determining that the preset pacing output is effective, and continuing to pace the patient using the preset pacing output, and simultaneously performing the R wave-triggered cardiac contractility modulation on the patient comprises:

judging whether the R wave has occurred in the second
 response information after the first pacing under the
 current pacing output, and if so, determining that the
 preset pacing output is effective, and continuing to pace
 the patient using the preset pacing output, and simul-
 taneously performing the R wave-triggered cardiac
 contractility modulation on the patient.

* * * * *